United States Patent
Delacourte et al.

(10) Patent No.: US 8,680,095 B2
(45) Date of Patent: Mar. 25, 2014

(54) HETEROCYCLE COMPOUNDS AND USES THEREOF FOR THE PREVENTION OR TREATMENT OF DISEASES INVOLVING FORMATION OF AMYLOID PLAQUES AND/OR WHERE A DYSFUNCTION OF THE APP METABOLISM OCCURS

(75) Inventors: Andre Delacourte, Faches-Thumesnil (FR); Patricia Melnyk, Lille Cedex (FR); Stephane Burlet, Croix (FR); Nicolas Lefur, Lille Cedex (FR)

(73) Assignees: Institut National de la Sante et de la Recherche Medicale (INSERM), Paris (FR); Universite Lille 2 Droit et Sante, Lille (FR); Centre National de la Recherche Scientifique (C.N.R.S.), Paris (FR); Universite Lille 1—Sciences et Technologies, Villeneuve-d'Ascq (FR)

( * ) Notice: Subject to any disclaimer, the term of this patent is extended or adjusted under 35 U.S.C. 154(b) by 0 days.

(21) Appl. No.: 13/515,570

(22) PCT Filed: Dec. 16, 2010

(86) PCT No.: PCT/EP2010/069897
§ 371 (c)(1),
(2), (4) Date: Jul. 17, 2012

(87) PCT Pub. No.: WO2011/073322
PCT Pub. Date: Jun. 23, 2011

(65) Prior Publication Data
US 2012/0283256 A1    Nov. 8, 2012

(30) Foreign Application Priority Data
Dec. 16, 2009    (EP) .................................... 09306242

(51) Int. Cl.
*A61K 31/4709* (2006.01)
*A61K 31/47* (2006.01)
*A61K 31/496* (2006.01)
*A61K 31/5377* (2006.01)
*A61P 25/28* (2006.01)

(52) U.S. Cl.
USPC ............... 514/232.5; 514/235.2; 514/252.11; 514/253.06; 514/313

(58) Field of Classification Search
None
See application file for complete search history.

(56) References Cited

U.S. PATENT DOCUMENTS

| 4,806,537 A | | 2/1989 | Roberts | |
|---|---|---|---|---|
| 5,242,932 A | * | 9/1993 | Gandy et al. | 514/313 |
| 2009/0203735 A1 | * | 8/2009 | Corfas et al. | 514/313 |

FOREIGN PATENT DOCUMENTS

EP    1283055    2/2003

OTHER PUBLICATIONS

Amyloid Plaque and Neurofibrillary Tangle Formation in Alzheimer's Disease, Cell Signaling Technology, Inc., (Jul. 2009).*
Delarue-Cochin et al: "Synthesis and antimalarial activity of new analogues of amodiaquine", European Journal of Medicinal Chemistry, vol. 43, No. 2, Feb. 1, 2008, pp. 252-260.

* cited by examiner

*Primary Examiner* — Janet L Andres
*Assistant Examiner* — Timothy R Rozof
(74) *Attorney, Agent, or Firm* — Whitham Curtis Christofferson & Cook, PC

(57) ABSTRACT

The present invention relates to compounds having the following Formula (I) for use in the prevention and/or the treatment of diseases involving formation of amyloid plaques and/or where a dysfunction of the APP metabolism occurs.

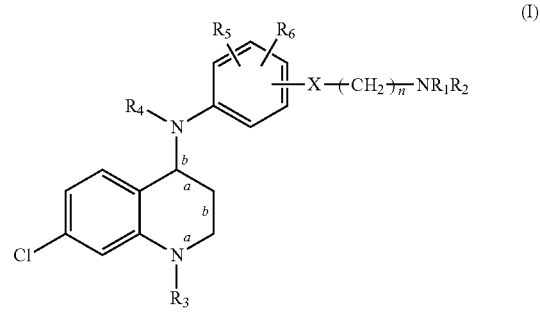

17 Claims, No Drawings

HETEROCYCLE COMPOUNDS AND USES THEREOF FOR THE PREVENTION OR TREATMENT OF DISEASES INVOLVING FORMATION OF AMYLOID PLAQUES AND/OR WHERE A DYSFUNCTION OF THE APP METABOLISM OCCURS

The present invention concerns new heterocycle compounds as well as uses thereof, for the prevention and/or the treatment of diseases involving formation of amyloid plaques and/or where a dysfunction of the APP metabolism occurs, such as Alzheimer's disease.

Alzheimer's disease is a progressive neurodegenerative disorder that gradually damages the neurons in regions of the brain involved in memory, learning and reasoning. It is characterized by extracellular accumulation of amyloid β (Aβ) peptides forming amyloid plaques in the brain. This accumulation of Aβ peptides in the brain has been shown to play a key role in the development of Alzheimer's disease.

Alzheimer's disease affects brain functions, including short-term memory loss, inability to reason, and the deterioration of language and the ability to care for oneself. An estimated 3% of people between the ages of 65 and 74 have Alzheimer's disease, rising to about half those age 85 and over.

WO 02/37118 discloses means for detecting pathological transformation of the amyloid protein precursor (APP) and their uses in diagnostic and therapeutic applications in degenerative pathologies such as Alzheimer's disease.

WO 2006/051489 discloses the use of 1,4-bis(3-aminoalkyl)piperazine derivatives for the treatment of neurodegenerative diseases, wherein said derivatives could be used to rectify the metabolism of the amyloid protein precursor (APP).

The aim of the invention is to provide new drugs for the treatment of diseases involving formation of amyloid plaques and/or where a dysfunction of the APP metabolism occurs, such as Alzheimer's disease.

The aim of the invention is to provide new compounds having the property of rectifying the metabolism of APP, wherein said compounds have an improved effect on said metabolism over prior art compounds.

The present invention relates to compounds having the following formula (I):

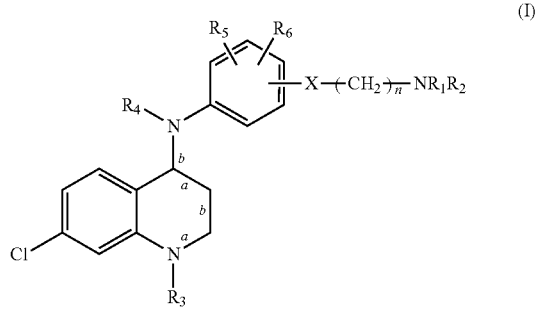

wherein:
a represents a single bond or a double bond;
b represents a single bond or a double bond, provided that when a is a single bond, then b is a double bond, and when a is a double bond, then b is a single bond;
$R_3$ is absent when a is a double bond, or, when a is a single bond, $R_3$ is chosen from the groups consisting of: alkyl, cycloalkyl, aryl and heterocyclyl radicals, said alkyl, cycloalkyl, aryl, and heterocyclyl radicals being possibly substituted;

$R_4$ is absent when b is a double bond, or, $R_4$ is H when b is a single bond;

$R_5$ is chosen from the group consisting of:
  H,
  $(C_1-C_{12})$alkyl,
  OH, and
  $(C_1-C_{12})$alkoxy, $R_6$ is chosen from the group consisting of:
  H,
  halogen, in particular F or Br,
  CN,
  OH,
  $(C_1-C_{12})$alkoxy,
  $(C_1-C_{12})$alkyl,
  $(C_6-C_{30})$aryl,
  heteroaryl,
  $CO_2R$, wherein R is an alkyl group comprising from 1 to 12 carbon atoms,
  $NR_aR_b$, $R_a$ and $R_b$ being each independently chosen from: H, alkyl, aralkyl, aryl, cycloalkyl, and heterocyclyl groups, said alkyl, aralkyl, aryl, cycloalkyl, and heterocyclyl groups being possibly substituted, or $R_a$ and $R_b$ forming together with the nitrogen atom carrying them a possibly substituted heterocyclyl group; and a radical of formula: $-X'-(CH_2)_{n'}-NR'_1R'_2$, wherein:
  X' is chosen from: $CH_2$, O, NH, CO, $CH_2OCO$, and NHCO;
  n' is 0, 1 or 2;
  $R'_1$ and $R'_2$ are each independently chosen from H, alkyl, aralkyl, aryl, cycloalkyl and heterocyclyl groups, said alkyl, aralkyl, aryl, cycloalkyl, and heterocyclyl groups being possibly substituted, or $R'_1$ and $R'_2$ may form together with the nitrogen atom carrying them a possibly substituted heterocyclyl group;

X is chosen from: $CH_2$, O, NH, CO, $CH_2OCO$, and NHCO;
n is 0, 1 or 2;
$R_1$ and $R_2$ are each independently chosen from H, alkyl, aralkyl, aryl, cycloalkyl and heterocyclyl groups, said alkyl, aralkyl, aryl, cycloalkyl and heterocyclyl groups being possibly substituted, or $R_1$ and $R_2$ may form together with the nitrogen atom carrying them a possibly substituted heterocyclyl group;

or its pharmaceutically acceptable salts, hydrates or hydrated salts or its polymorphic crystalline structures, racemates, diastereisomers or enantiomers, for use in the prevention and/or the treatment of diseases involving formation of amyloid plaques and/or where a dysfunction of the APP metabolism occurs, with the exclusion of the compounds having the following formula:

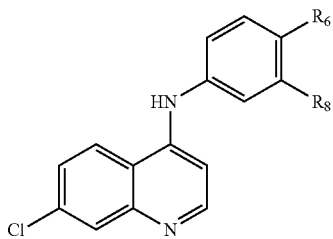

wherein:
$R_6$ is H and $R_8$ is —$CH_2$—$NEt_2$;
$R_6$ is OH and $R_8$ is chosen from: —$CH_2$—$NEt_2$, —$CH_2$—$NHEt$,

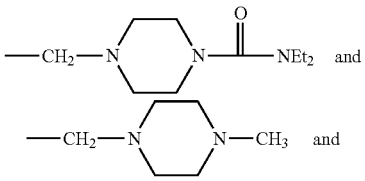

$R_6$ is OMe and $R_8$ is —$CH_2$—$NEt_2$ or

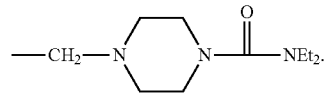

The term "alkyl" means a saturated or unsaturated aliphatic hydrocarbon group which may be straight or branched having 1 to 12 carbon atoms in the chain. Preferred alkyl groups have 1 to 6 carbon atoms in the chain. "Branched" means that one or lower alkyl groups such as methyl, ethyl or propyl are attached to a linear alkyl chain. <<Lower alkyl>> means 1 to 4 carbon atoms in the chain which may be straight or branched. The alkyl may be substituted with one or more <<alkyl group substituants>> which may be the same or different, and include for instance halo, cycloalkyl, hydroxy, alkoxy, amino, acylamino, aroylamino, carboxy.

The term "halo" refers to the atoms of the group 17 of the periodic table (halogens) and includes in particular fluorine, chlorine, bromine, and iodine atom.

The terms "arylalkyl" or "aralkyl" refer to an alkyl moiety in which an alkyl hydrogen atom is replaced by an aryl group. Examples of "arylalkyl" or "aralkyl" include benzyl and 9-fluorenyl groups.

The term "cycloalkyl" as employed herein includes saturated cyclic, bicyclic, tricyclic, or polycyclic hydrocarbon groups having 3 to 12 carbons, wherein any ring atom capable of substitution may be substituted by a substituent. Examples of cycloalkyl moieties include, but are not limited to, cyclohexyl and adamantyl.

The term "aryl" refers to an aromatic monocyclic, bicyclic, or tricyclic hydrocarbon ring system, wherein any ring atom capable of substitution may be substituted by a substituent. Examples of aryl moieties include, but are not limited to, phenyl, naphthyl, and anthracenyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e. g., carbon atoms and 1-3, 1-6, or 1-9 heteroatoms of N, O, or S if monocyclic, bicyclic, or tricyclic, respectively), wherein any ring atom capable of substitution may be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e. g., carbon atoms and 1-3, 1-6, or 1-9 heteroatoms of N, O, or S if monocyclic, bicyclic, or tricyclic, respectively), wherein any ring atom capable of substitution may be substituted by a substituent.

The term "alkoxy" refers to an —O-alkyl radical.

The term "substituents" refers to a group "substituted" on an alkyl, cycloalkyl, heterocyclyl, aryl, aralkyl or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "oxo" refers to an oxygen atom, which forms a carbonyl when attached to carbon, an N-oxide when attached to nitrogen, and a sulfoxide or sulfone when attached to sulfur.

The term "alkenyl" as employed herein includes partially unsaturated, nonaromatic, hydrocarbon groups having 2 to 12 carbons, preferably 2 to 6 carbons.

The term "alkylene" as employed herein refers to a divalent radical comprising from 1 to 12 carbon atoms, and preferably from 1 to 6 carbon atoms. Said radical may be represented by the formula $(CH_2)_n$ wherein n is an integer varying from 1 to 12, and preferably from 1 to 6.

The compounds herein described may have asymmetric centers. Compounds of the present invention containing an asymmetrically substituted atom may be isolated in optically active or racemic forms. It is well-known in the art how to prepare optically active forms, such as by resolution of racemic forms or by synthesis from optically active starting materials. All chiral, diastereomeric, racemic forms and all geometric isomeric forms of a compound are intended, unless the stereochemistry or the isomeric form is specifically indicated.

"Pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable salt" refers to salts which retain the biological effectiveness and properties of the compounds of the invention and which are not biologically or otherwise undesirable. In many cases, the compounds of the invention are capable of forming acid and/or base salts by virtue of the presence of amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) J. Pharm. Sd, vol. 66, 1). The expression "non-toxic pharmaceutically acceptable salts" refers to non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

In the context of the invention, the term "treating" or "treatment", as used herein, means reversing, alleviating, inhibiting the progress of, or preventing the disorder or condition to which such term applies, or one or more symptoms of such disorder or condition.

While it is possible for the compounds of the invention having formula (I) to be administered alone it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and optionally other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Total daily dose of the compounds of the invention administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Unexpectedly, the inventors have discovered that the compounds of formula (I) according to the present invention could be used to rectify the metabolism of the Amyloid Protein Precursor (APP) on three essential points:

1) increasing the carboxy-terminal fragments of APP (APP-CTFs) which all in common possess the last 50 aminoacids of APP, and especially those having potential physiological activities, such as the α-stubs (APP-CTFs α) and the AICD (APP intra cellular domain) with neurotrophic properties, 2) decreasing the production of the neurotoxic by-products of APP, i.e. β-amyloid (Aβ) peptides, especially in their form 1-40 and 1-42, Therefore, the compounds of formula (I) as described herein are useful in the treatment of all diseases where a dysfunction of the APP metabolism occurs. These diseases also include pathologies involving amyloid depot.

Among those diseases, one may in particular mention such as Alzheimer's disease, Lewy body disease, Down syndrome, amyloid angiopathy, Parkinson's disease, prion diseases, in particular Creutzfeldt-Jakob Disease (CJD), amyotrophic lateral sclerosis (ALS), and frontotemporal degeneration.

In formula (I) mentioned above, when $R_6$ is a radical $-X'-(CH_2)_{n'}-NR'_1R'_2$, said radical may be identical to or different from the radical $-X-(CH_2)_n-NR_1R_2$.

The present invention also relates to compounds of formula (I-1):

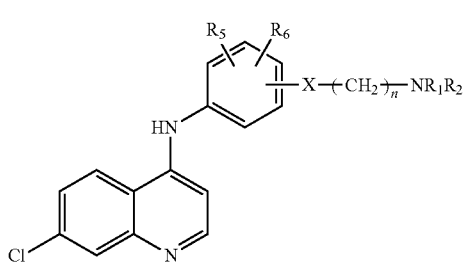

wherein $R_1$, $R_2$, $R_5$, $R_6$, X, and n are as defined above in formula (I), for use in the prevention and/or the treatment of diseases involving formation of amyloid plaques and/or where a dysfunction of the APP metabolism occurs.

The compounds of formula (I-1) are compounds of formula (I) wherein a is a double bond and b is a single bond, $R_3$ is none and $R_4$ is H.

The present invention also relates to the compounds of formula (I) for the use as mentioned above, wherein $R_5$ is H.

The present invention also relates to the compounds of formula (I) for the use as mentioned above, wherein $R_1$ and $R_2$ are ethyl.

The present invention also relates to the compounds of formula (I) for the use as mentioned above, wherein $R_1$ and $R_2$ form together with N a pyrrolidine group.

The present invention also relates to the compounds of formula (I) for the use as mentioned above, wherein —$NR_1R_2$ is chosen from the group consisting of: —$NEt_2$, —NHtBu, pyrrolidinyl, morpholinyl, and N-methyl-piperazinyl.

The present invention also relates to the compounds of formula (I) for the use as mentioned above, wherein $R_6$ is halogen, and preferably F.

The present invention also relates to compounds of formula (I-2):

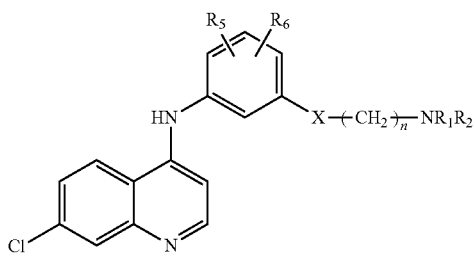

wherein $R_1$, $R_2$, $R_5$, $R_6$, X, and n are as defined above in formula (I), for use in the prevention and/or the treatment of diseases involving formation of amyloid plaques and/or where a dysfunction of the APP metabolism occurs.

The present invention also relates to compounds of formula (I-3):

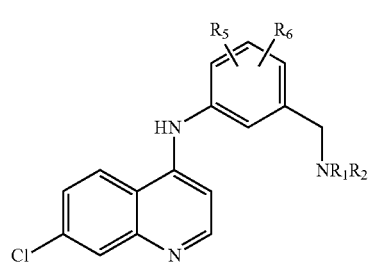

wherein $R_1$, $R_2$, $R_5$, and $R_6$ are as defined above in formula (I), for use in the prevention and/or the treatment of diseases involving formation of amyloid plaques and/or where a dysfunction of the APP metabolism occurs.

The compounds of formula (I-3) are compounds of formula (I-2) wherein X is $CH_2$ and n is 0.

The present invention also relates to compounds of formula (I-4):

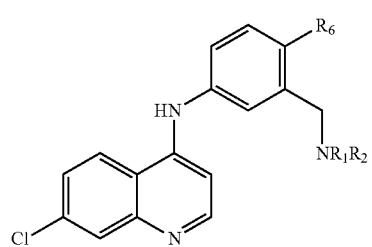

Preferably, the present invention relates to compounds of formula (I-4) as defined above, for use in the prevention and/or the treatment of diseases involving formation of amyloid plaques and/or where a dysfunction of the APP metabolism occurs, wherein when $R_6$ is OH, then $R_1$ and $R_2$ are not ethyl.

Preferably, the present invention relates to compounds of formula (I-4) as defined above, for use in the prevention and/or the treatment of diseases involving formation of amyloid plaques and/or where a dysfunction of the APP metabolism occurs, wherein $R_6$ is halogen, and preferably F, or alkyl.

A particular class of compounds which may be used in the present invention is constituted of compounds having the following formula (I-4-1):

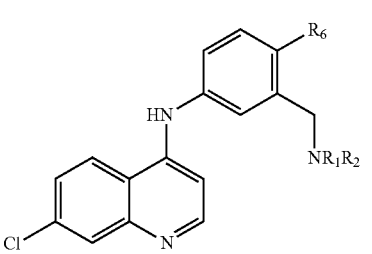

wherein $R_1$ and $R_2$ are as defined above in formula (I), and $R_6$ is chosen from: H, OH, and ($C_1$-$C_{12}$)alkoxy.

In formula (I-4-1), $R_6$ is preferably chosen from H, OH and OEt.

In formula (I-4-1), $R_1$ and $R_2$ are preferably ethyl or form together with N a pyrrolidine group.

Preferably, in formula (I-4-1), when $R_6$ is OH, then $R_1$ and $R_2$ are not ethyl, or $R_1$ and $R_2$ do not form together with N a N-methyl-piperazinyl group. Preferably, in formula (I-4-1), when $R_6$ is methoxy, then $R_1$ and $R_2$ are not ethyl.

Thus, a particularly preferred class of compounds which may be used in the present invention is constituted of compounds having the following formula (I-4-1-1):

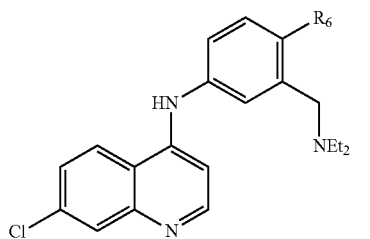

(I-4-1-1)

wherein $R_6$ is as defined above, and is preferably chosen from H, OH and OEt.

Another particularly preferred class of compounds which may be used in the present invention is constituted of compounds having the following formula (I-4-1-2):

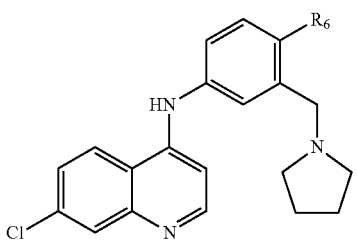

(I-4-1-2)

wherein $R_6$ is as defined above, and is preferably chosen from H, OH and OEt.

A particular class of compounds which may be used in the present invention is constituted of compounds having the following formula (I-4-2):

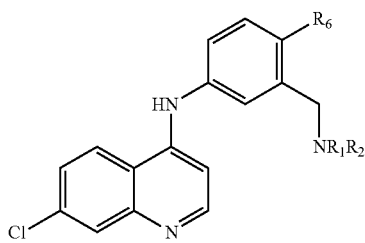

(I-4-2)

wherein $R_1$ and $R_2$ are as defined above in formula (I), and $R_6$ is chosen from: $(C_1-C_{12})$alkyl, $(C_6-C_{30})$aryl, and heteroaryl, said alkyl, aryl and heteroaryl being possibly substituted.

In formula (I-4-2), $R_1$ and $R_2$ are preferably ethyl or form together with N a pyrrolidine group.

In formula (I-4-2), $R_6$ is preferably Me, Et, furyl, thienyl, or a possibly substituted phenyl group. Among the substituents, the followings may be cited: alkyl such as $CH_3$ or tBu, perfluoroalkyl such as $CF_3$, halogen such as F or Cl, alkoxy such as $OCH_3$, aryloxy such as OBn, alkylcarbonyl such as $COCH_3$, and perfluoroalkoxy such as $OCF_3$.

Thus, a particularly preferred class of compounds which may be used in the present invention is constituted of compounds having the following formula (I-4-2-1):

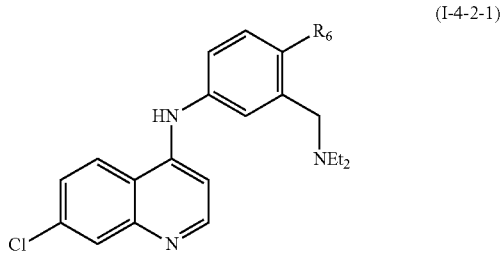

(I-4-2-1)

wherein $R_6$ is as defined above in formula (I-4-2).

Another particularly preferred class of compounds which may be used in the present invention is constituted of compounds having the following formula (I-4-2-2):

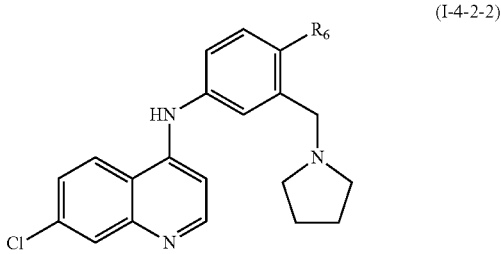

(I-4-2-2)

wherein $R_6$ is as defined above in formula (I-4-2).

Another particularly preferred class of compounds which may be used in the present invention is constituted of compounds having the following formula (I-4-2-3):

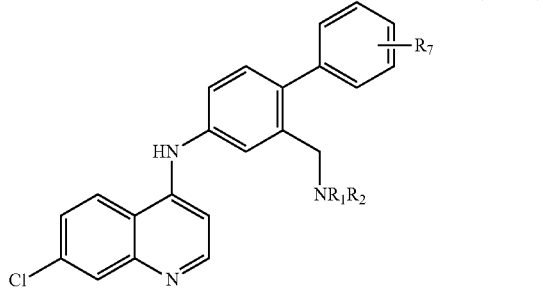

(I-4-2-3)

wherein $R_1$ and $R_2$ are as defined above in formula (I), and $R_7$ is chosen from alkyl such as $CH_3$ or tBu, perfluoroalkyl such as $CF_3$, halogen such as F or Cl, alkoxy such as $OCH_3$, aryloxy such as OBn, alkylcarbonyl such as $COCH_3$, and perfluoroalkoxy such as $OCF_3$.

A particular class of compounds which may be used in the present invention is constituted of compounds having the following formula (I-4-3):

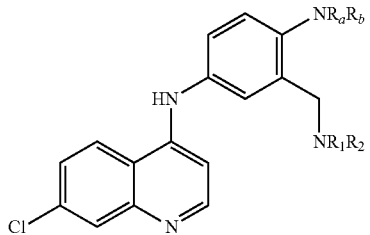

(I-4-3)

wherein $R_a$, $R_b$, $R_1$ and $R_2$ are as defined above in formula (I).

In formula (I-4-3), $R_1$ and $R_2$ are preferably ethyl or form together with N a pyrrolidine group.

Preferably, in formula (I-4-3), $R_a$ and $R_b$ form together with the nitrogen atom carrying them a morpholinyl or a N-methyl-piperazinyl group.

A particular class of compounds which may be used in the present invention is constituted of compounds having the following formula (I-4-4):

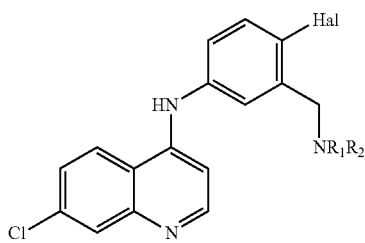

(I-4-4)

wherein $R_1$ and $R_2$ are as defined above in formula (I).

Preferably, in formula (I-4-4), $R_6$ is Br or F, and most preferably F.

Preferably, in formula (I-4-4), $R_1$ and $R_2$ are preferably ethyl or form together with N a pyrrolidine group.

The present invention also relates to compounds of formula (I-3-1):

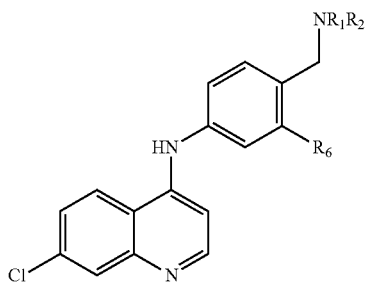

(I-3-1)

wherein $R_1$, $R_2$ and $R_6$ are as defined above in formula (I), for use in the prevention and/or the treatment of diseases involving formation of amyloid plaques and/or where a dysfunction of the APP metabolism occurs.

Preferably, in formula (I-3-1), $R_6$ is OH.

The present invention also relates to compounds of formula (I-3-2):

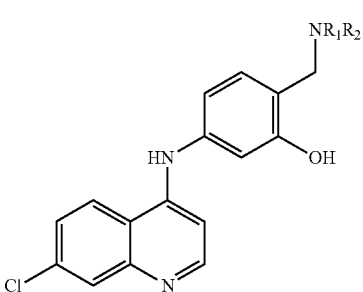

(I-3-2)

wherein $R_1$ and $R_2$ are as defined above in formula (I), for use in the prevention and/or the treatment of diseases involving formation of amyloid plaques and/or where a dysfunction of the APP metabolism occurs.

Preferably, in formula (I-3-1) or (I-3-2), —$NR_1R_2$ is chosen from the group consisting of: —$NEt_2$, —NHtBu, pyrrolidinyl, morpholinyl, and N-methyl-piperazinyl.

The present invention also relates to compounds of formula (I-5):

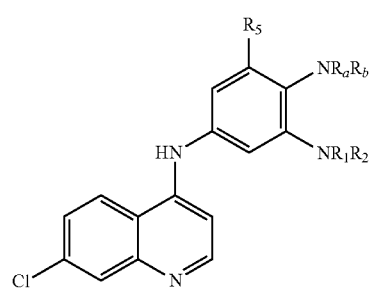

(I-5)

wherein $R_1$, $R_2$, $R_5$, $R_a$ and $R_b$ are as defined in formula (I), $R_5$ being preferably H or $CH_3$, $R_a$ and $R_b$ preferably forming with the nitrogen atom carrying them a possibly substituted heterocyclyl group, and more preferably $R_a$ and $R_b$ forming with the nitrogen atom carrying them a N-methylpiperazine or a morpholine group, for use in the prevention and/or the treatment of diseases involving formation of amyloid plaques and/or where a dysfunction of the APP metabolism occurs.

According to a preferred embodiment, in above formula (I-5), $R_5$ is H.

According to another preferred embodiment, in above formula (I-5), $R_5$ is $CH_3$.

The present invention also relates to compounds of formula (I-6):

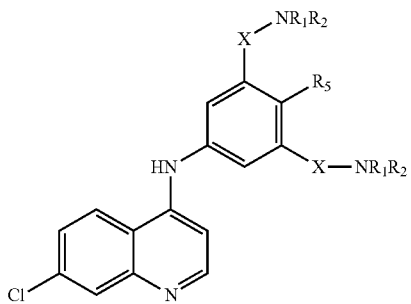

wherein $R_1$, $R_2$ and $R_5$ are as defined in formula (I),
and wherein X is CO or $CH_2$)

$R_5$ being preferably H or OH, and more preferably H, for use in the prevention and/or the treatment of diseases involving formation of amyloid plaques and/or where a dysfunction of the APP metabolism occurs.

According to a preferred embodiment, in above formula (I-6), $R_5$ is H.

According to another preferred embodiment, in above formula (I-6), $R_5$ is OH.

A particular class of compounds which may be used in the present invention is constituted of compounds having the following formula (I-6-1):

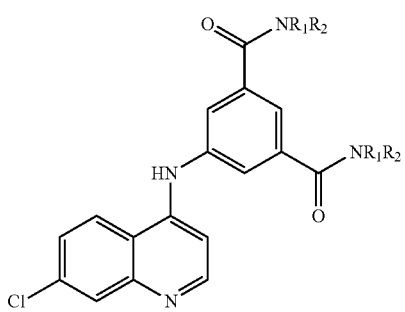

Compounds of formula (I-6-1) correspond to compounds having formula (I-6) wherein $R_5$ is H and X is CO.

A particular class of compounds which may be used in the present invention is constituted of compounds having the following formula (I-6-2):

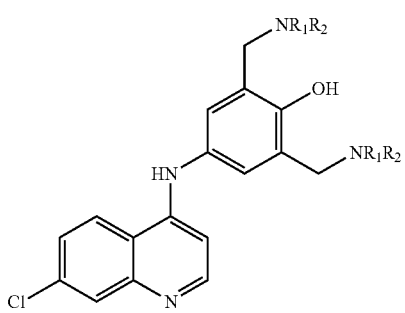

Compounds of formula (I-6-2) correspond to compounds having formula (I-6) wherein $R_5$ is OH and X is $CH_2$.

Preferably, in formula (I-6-2), $R_1$ and $R_2$ form together with the nitrogen atom carrying them a pyrrolidinyl, a N-methylpiperazinyl or a morpholinyl group.

A particular class of compounds which may be used in the present invention is constituted of compounds having the following formula (I-7):

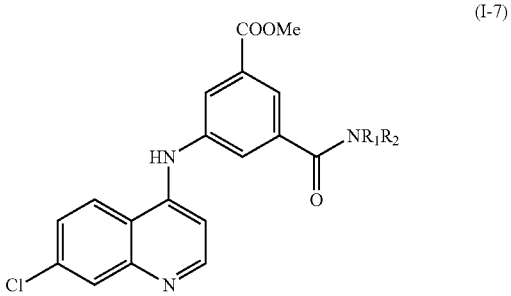

wherein $R_1$ and $R_2$ are as defined in formula (I).

The present invention also relates to compounds of formula (I-8):

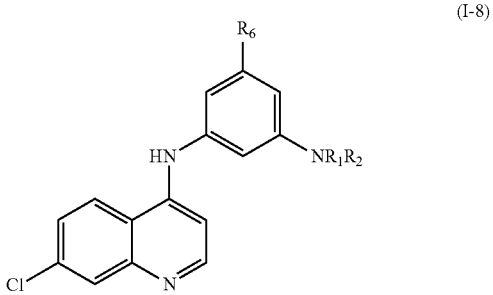

wherein $R_1$ and $R_2$ are as defined in formula (I), and form together with the nitrogen atom carrying them a heterocycle, and $R_6$ is as defined in formula (I), for use in the prevention and/or the treatment of diseases involving formation of amyloid plaques and/or where a dysfunction of the APP metabolism occurs.

The present invention also relates to compounds of formula (I-9):

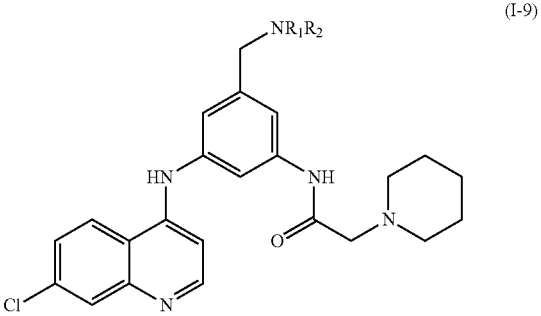

wherein $R_1$ and $R_2$ are as defined in formula (I), for use in the prevention and/or the treatment of diseases involving formation of amyloid plaques and/or where a dysfunction of the APP metabolism occurs.

The present invention also relates to compounds of formula (I-10):

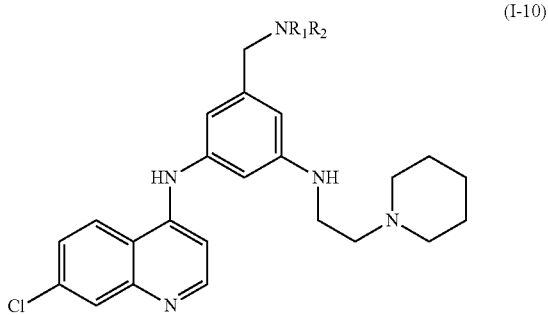

wherein $R_1$ and $R_2$ are as defined in formula (I), for use in the prevention and/or the treatment of diseases involving formation of amyloid plaques and/or where a dysfunction of the APP metabolism occurs.

The present invention also relates to compounds of formula (I-11):

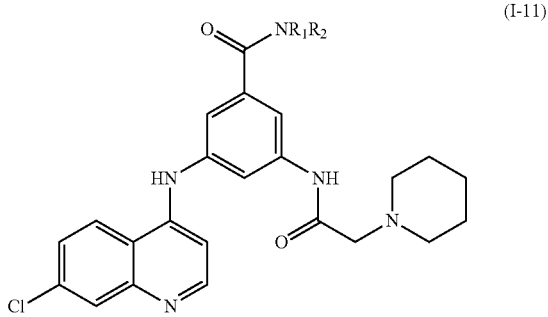

wherein $R_1$ and $R_2$ are as defined in formula (I), for use in the prevention and/or the treatment of diseases involving formation of amyloid plaques and/or where a dysfunction of the APP metabolism occurs.

The present invention also relates to compounds of formula (I-12):

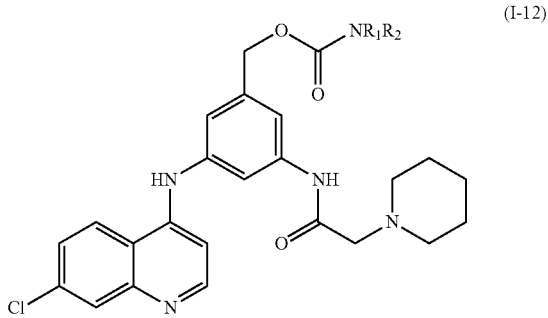

wherein $R_1$ and $R_2$ are as defined in formula (I), for use in the prevention and/or the treatment of diseases involving formation of amyloid plaques and/or where a dysfunction of the APP metabolism occurs.

Some of the compounds of formula (I) are already known. Indeed, various compounds of formula (I) are useful for their antimalarial properties.

In particular, compounds of formula (I-4) are disclosed in (a) <<Synthesis and Antimalarial Activity of New Analogues of Amodiaquine>>, Delarue-Cochin, S.; Paunescu, E.; Maes, L.; Mouray, E.; Sergheraert, C.; Grellier, P.; Melnyk, P. *European Journal of Medicinal Chemistry* 2008, 43, 252-260, (b) <<Replacement of 4'-hydroxy group of Amodiaquine and Amopyroquine by aromatic and aliphatic substituants: Synthesis and Antimalarial Activity>>, Paunescu, E.; Susplugas, S.; Boll, E.; Varga, R.; Mouray, E.; Grosu, I.; Grellier, P.; Melnyk, P., *ChemMedChem*. 2009, 4 (4), 549-561; (c) <<Suzuki coupling reaction as the key step for the synthesis of 4'-substituted analogues of Amodiaquine>>, Paunescu, E.; Matuszak, N.; Melnyk, P., *Tetrahedron* 2007, 63, 12791-12810; and (d) <<Synthesis and Antimalarial Activity of New Amino Analogues of Amodiaquine and Amopyroquine>>, Paunescu, E.; Susplugas, S.; Boll, E.; Vargas, R. A.; Mouray, E.; Grellier, P.; Melnyk, P., *Medicinal Chemistry* 2008, 4 (5), 407-425.

In particular, compounds of formula (I-9) are disclosed in <<Synthesis and in vitro and in vivo Antimalarial Activity of New 4-aminoquinolines>>, Delarue-Cochin, S.; Girault, S.; Maes, L.; Debreu-Fontaine, M.-A.; Labaeïd, M.; Grellier, P.; Sergheraert, C., *Journal of Medicinal Chemistry* 2001, 44, 2827-2833.

In particular, compounds of formula (I-10) are disclosed in <<Synthesis and in vitro and in vivo Antimalarial Activity of New 4-aminoquinolines>>, Delarue-Cochin, S.; Girault, S.; Maes, L.; Debreu-Fontaine, M.-A.; Labaeïd, M.; Grellier, P.; Sergheraert, C., *Journal of Medicinal Chemistry* 2001, 44, 2827-2833; and in <<Synthesis and Antimalarial Activity of New Analogues of Amodiaquine>>, Delarue-Cochin, S.; Paunescu, E.; Maes, L.; Mouray, E.; Sergheraert, C.; Grellier, P.; Melnyk, P. *European Journal of Medicinal Chemistry* 2008, 43, 252-260.

In particular, compounds of formulae (I-11) and (I-12) are disclosed in <<Synthesis and Antimalarial Activity of Carbamate and Amide Derivatives of 4-anilinoquinoline>>, Delarue-Cochin, S.; Grellier, P.; Maes, L.; Mouray, E.; Sergheraert, C.; Melnyk, P., *European Journal of Medicinal Chemistry*. 2008, 43, 2045-2055.

Some of the compounds of formula (I) are new compounds: compounds having formulae (I-5), (I-6) wherein $R_5$=H, (I-7), and (I-8) as defined above have never been disclosed.

The present invention also relates to compounds having following formula (I-5-1):

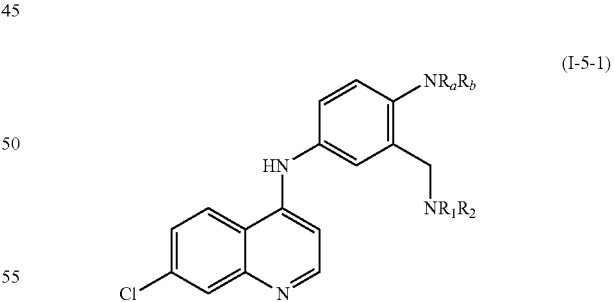

wherein $R_1$, $R_2$, $R_a$ and $R_b$ are as defined in formula (I), $R_a$ and $R_b$ preferably forming with the nitrogen atom carrying them a possibly substituted heterocyclyl group, and more preferably $R_a$ and $R_b$ forming with the nitrogen atom carrying them a N-methylpiperazine or a morpholine group.

Preferably, in formula (I-5-1), $R_1$ and $R_2$ form together with the nitrogen atom carrying them a N-methylpiperazinyl group or $R_1$ and $R_2$ are ethyl.

The present invention also relates to compounds having following formula (I-5-2) or (I-5-3):

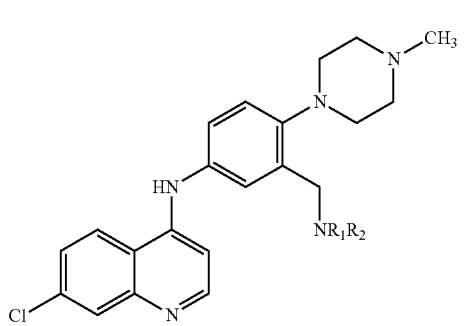

(I-5-2)

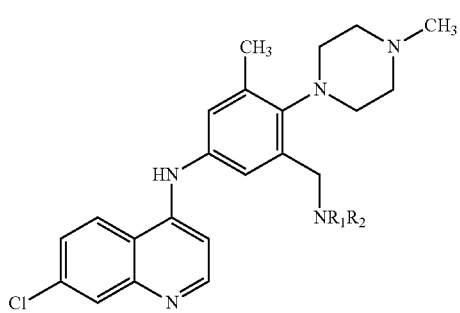

(I-5-3)

wherein $R_1$ and $R_2$ are as defined in formula (I).

The present invention also relates to compounds having following formula (I-5-4):

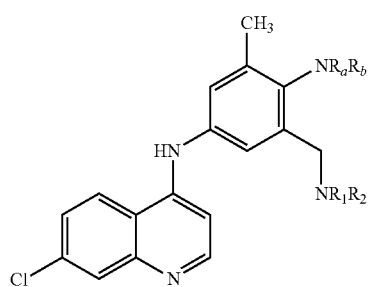

(I-5-4)

wherein $R_1$, $R_2$, $R_a$ and $R_b$ are as defined in formula (I), $R_a$ and $R_b$ preferably forming with the nitrogen atom carrying them a possibly substituted heterocyclyl group, and more preferably $R_a$ and $R_b$ forming with the nitrogen atom carrying them a N-methylpiperazine or a morpholine group.

Preferred classes of compounds consist of compounds having formulae (I-6-1) or (I-6-2) as follows:

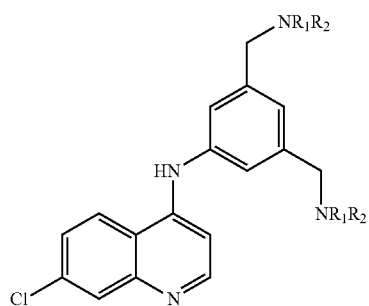

(I-6-1)

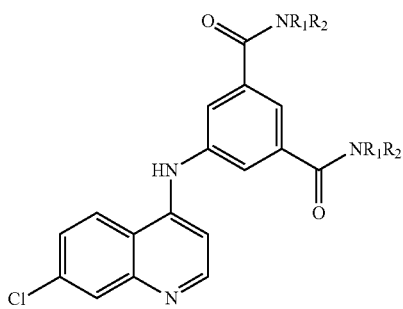

(I-6-2)

wherein $R_1$ and $R_2$ are as defined in formula (I).

Preferred classes of compounds consist of compounds having formulae (I-8-1) or (I-8-2) as follows:

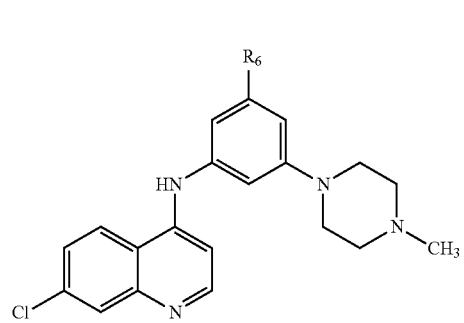

(I-8-1)

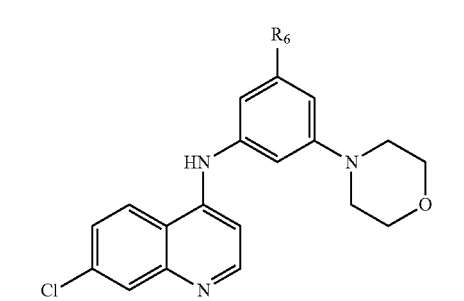

(I-8-2)

$R_6$ being as defined in formula (I).

Another preferred class of compounds consists of compounds having formula (I-8-3) as follows

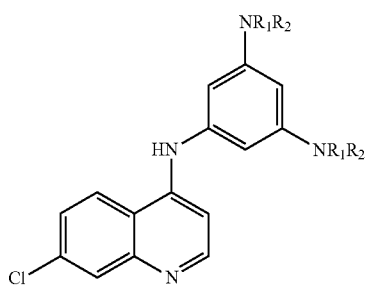

(I-8-3)

$R_1$ and $R_2$ being as defined in formula (I).

The present invention also relates to compounds of formula (I-13):

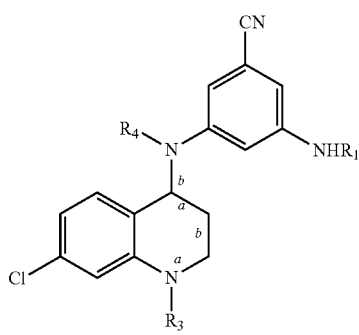
(I-13)

a, b, $R_3$, $R_1$ and $R_4$ being as defined in formula (I).

A preferred class of compounds of the invention consists of compounds having formula (I-13-1):

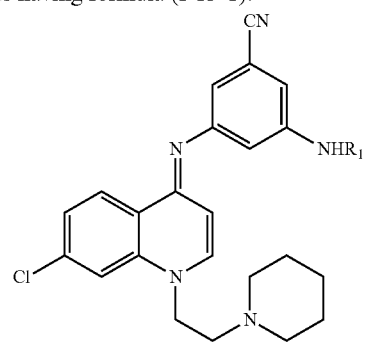
(I-13-1)

$R_1$ being as defined in formula (I),
$R_1$ representing preferably H or

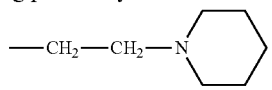

The present invention also relates to a pharmaceutical composition comprising the compounds having formulae (I-5), (I-5-1), (I-5-2), (I-5-3), (I-5-4), (I-6), (I-6-1), (I-6-2), (I-8), (I-8-1), (I-8-2), (I-8-3), (I-13), and (I-13-1) as defined above, in association with a pharmaceutically acceptable vehicle.

The compounds of formula (I) have the property of decreasing the secretion of the Aβ peptide (80% at 1 μM, and almost no secretion at 5 μM), and of increasing the production of APP-CTF alpha stubs and AICD (×30-40 at 5 μM).

The present invention also relates to a method for the preparation of compounds having formula (I-8-3) as defined above, said method comprising the following steps:

a) a step of reacting 3,5-dibromobenzene with a compound having formula $HNR_1R_2$, $R_1$ and $R_2$ being as defined in formula (I), to obtain a compound having the following formula (I-8-3-1):

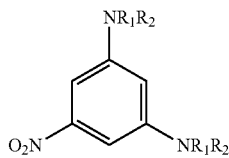
(I-8-3-1)

b) a step of hydrogenating the compound of formula (I-8-3-1) to obtain a compound having the following formula (I-8-3-2):

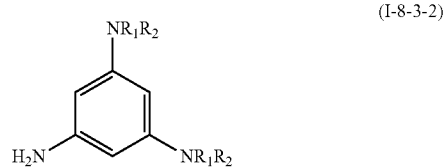
(I-8-3-2)

c) and a step of reacting the compound of formula (I-8-3-2) with 4,7-dichloroquinoline to obtain the compound of formula (I-8-3), said step being possibly followed by a step of recovering said compound.

Preferably, 3,5-dibromobenzene is prepared from 2,6-dibromo-4-nitroanaline, which is in particular prepared from p-nitroaniline (Sheperd et al., 1947).

Preferably, step a) is carried out in the presence of BINAP (2,2'-bis(diphenylphosphino)-1,1'-binaphthyl), $Cs_2CO_3$, $Pd_2dba_3$ (tris(dibenzylidene-acetone)dipalladium(0)) and dry 1,4-dioxane.

Preferably, hydrogenation step b) is carried out in the presence of ammonium formate and Pd/C in EtOH.

Preferably, step c) is carried out in the presence of BINAP, $Cs_2CO_3$, $Pd_2dba_3$ and dry 1,4-dioxane.

EXPERIMENTAL PART

A—Synthesis of the New Compounds

General Procedure A: $AlMe_3$ Promoted Amide Formation

A solution of $AlMe_3$ (2M in toluene, n eq) was added dropwise to a solution of the appropriate amine (n eq) in anhydrous DCM at 0° C. The reaction mixture was stirred for 30 min and then allowed to warm up to room temperature. 1,3-Dimethyl 5-[(7-chloroquinolin-4-yl)amino]benzene-1,3-dicarboxylate 1 was added portionwise and the reaction mixture was refluxed for 24 h. The mixture was then poured in crushed ice and evaporated. The residue was suspended in a DCM/methanol mixture and the precipitate was removed by filtration. The filtrate was evaporated and purified by TLC.

Example 1

Preparation of 7-chloro-N-[4-(4-methylpiperazin-1-yl)-3-[(4-methylpiperazin-1-yl)methyl]phenyl]quinolin-4-amine (compound 55)

Step A:
[2-(4-Methylpiperazin-1-yl)-5-nitrophenyl]methanol

2-Fluoro-5-nitrobenzyl alcohol (1 g, 5.84 mmol) and N-methylpiperazine (1.29 mL, 2 eq) were heated at 130° C. for 1 h. The reaction mixture was then diluted with 25 mL of THF and washed with a saturated aqueous solution of $Na_2CO_3$ and then with brine. The organic layer was dried over $Na_2SO_4$, filtered and evaporated. The residue was thoroughly washed with pentane and filtered off to yield expected compound as an orange powder (1.38 g, 94% yield). m/z (ESI) 252.1 $[M+H]^+$.

$^1$H NMR (300 MHz, MeOH-$d_4$) δ8.46; (d, J=2.8 Hz, 1H), 8.18; (dd, J=8.9 and 2.9 Hz, 1H), 7.26; (d, J=8.90 Hz, 1H), 4.75; (s, 2H), 3.20-3.10; (m, 4H), 2.75-2.65; (m, 4H), 2.44; (s, 3H); $^{13}$C NMR (75 MHz, MeOH-$d_4$) δ156.5; (C), 143.4; (C), 136.6; (C), 124.1; (CH), 123.6; (CH), 119.0; (CH), 59.5; ($CH_2$), 55.2; ($CH_2$), 51.7; ($CH_2$), 45.2; ($CH_3$).

Step B: 1-methyl-4-{2-[(4-methylpiperazin-1-yl)methyl]-4-nitrophenyl}piperazine To [2-(4-methylpiperazin-1-yl)-5-nitrophenyl]methanol (0.150 g, 0.60 mmol) in 5 mL of THF at 0° C. was added thionyl chloride (0.22 mL, 5 eq). The reaction mixture was refluxed for 45 minutes and then the solvent and the excess of thionyl chloride were evaporated. The residue was suspended in 5 mL of acetonitrile and 1-methylpiperazine (0.33 mL, 5 eq) was added at 0° C. The solution was stirred overnight at room temperature, evaporated and the residue was dissolved in ethyl acetate and washed with a saturated aqueous solution of $Na_2CO_3$. The aqueous layer was extracted with ethyl acetate and then the combined organic layers were dried over $Na_2SO_4$, filtered and evaporated. The residue was thoroughly washed with pentane and filtered off to yield expected compound as an orange powder (0.185 g, 92% yield).

$^1$H NMR (300 MHz, $CDCl_3$) δ 8.23; (d, J=2.8 Hz, 1H), 7.96; (dd, J=8.9 and 2.8 Hz, 1H), 6.94; (d, J=8.9 Hz, 1H), 3.40; (s, 2H), 3.10-3.00; (m, 4H), 2.60-2.25; (m, 12H), 2.27; (s, 3H), 2.19; (s, 3H).

Step C: 4-(4-methylpiperazin-1-yl)-3-[(4-methylpiperazin-1-yl)methyl]aniline A mixture of $SnCl_2$ (0.398 g, 2.1 mmol), 1.6 mL of HCl 1M and 5 mL of THF was added to a solution of 1-methyl-4-{2-[(4-methylpiperazin-1-yl)methyl]-4-nitrophenyl}piperazine (0.175 g, 2.5 eq) in 15 mL of THF. The reaction mixture was refluxed for 3 h and allowed to cool to room temperature. A saturated aqueous solution of $Na_2CO_3$ was added. The aqueous layer was extracted with DCM. The combined organic layers were dried over $Na_2SO_4$, filtered and evaporated. The residue was purified by flash chromatography (DCM/MeOH/$NH_4OH$//8/2/0.1) to yield expected compound as a brown oil (100 mg, 63% yield).

$^1$H NMR (300 MHz, $CDCl_3$) δ 6.89; (d, J=8.4 Hz, 1H), 6.71; (d, J=2.7 Hz, 1H), 6.51; (dd, J=8.9 and 3.0 Hz, 1H), 3.45; (s, 2H), 2.83; (t, J=4.8 Hz, 4H), 2.60-2.30; (m, 12H), 2.28; (s, 3H), 2.22; (s, 3H); $^{13}$C NMR (75 MHz, $CDCl_3$) δ 144.2; (C), 142.5; (C), 134.7; (C), 121.4; (CH), 117.4; (CH), 114.4; (CH), 57.3; ($CH_2$), 55.9; ($CH_2$), 55.3; ($CH_2$), 53.1; ($CH_2$), 53.1; ($CH_2$), 46.2; ($CH_3$), 46.1; ($CH_3$).

Step D: 7-chloro-N-[4-(4-methylpiperazin-1-yl)-3-[(4-methylpiperazin-1-yl)methyl]phenyl]quinolin-4-amine 4-(4-methylpiperazin-1-yl)-3-[(4-methylpiperazin-1-yl)methyl]aniline (68 mg, 0.22 mmol) and 4,7-dichloroquinoline (44 mg, 1 eq) were refluxed overnight in 10 mL of acetonitrile with 0.66 mL of HCl 1M. The reaction mixture was then evaporated and purified by preparative thin-layer chromatography (DCM/MeOH/$NH_4O$/18/210.1) to yield expected compound as a pale yellow solid (49 mg, 48% yield). m/z (ESI) 465.2 $[M+H]^+$.

$^1$H NMR (300 MHz, MeOH-$d_4$) δ 8.37; (d, J=5.6 Hz, 1H), 8.31; (d, J=9.1 Hz, 1H), 7.88; (d, J=2.1 Hz, 1H), 7.53; (dd, J=9.1 and 2.1 Hz, 1H), 7.47; (s, 1H), 7.33-7.26; (m, 2H), 6.84; (d, J=5.6 Hz, 1H), 3.68; (s, 2H), 3.76; (s, 2H), 3.12-3.00; (m, 4H), 2.85-2.45; (m, 12H), 2.42; (s, 3H), 2.33; (s, 3H); $^{13}$C NMR (75 MHz, MeOH-$d_4$) δ 154.1; (C), 149.8; (C), 145.8; (CH), 142.5; (C), 138.8; (C), 134.5; (C), 134.5; (C), 127.6; (CH), 127.3; (CH), 125.1; (CH), 125.1; (CH), 122.2; (CH), 121.7; (CH), 116.9; (C), 100.8; (CH), 56.5; ($CH_2$), 54.6; ($CH_2$), 53.9; ($CH_2$), 50.4; ($CH_2$), 50.0; ($CH_2$), 42.8; ($CH_3$), 42.6; ($CH_3$).

Example 2

Preparation of N-{3-[(tert-butylamino)methyl]-4-(4-methyl piperazin-1-yl)phenyl}-7-chloroquinolin-4-amine (compound 56)

Step A: tert-butyl({[2-(4-methylpiperazin-1-yl)-5-nitrophenyl]methyl})amine

To [2-(4-methylpiperazin-1-yl)-5-nitrophenyl]methanol prepared in step A of example 1 (0.150 g, 0.60 mmol) in 5 mL of THF at 0° C. was added thionyl chloride (0.22 mL, 5 eq). The reaction mixture was refluxed for 45 minutes and then the solvent and the excess of thionyl chloride were evaporated. The residue was suspended in 5 mL of acetonitrile and tert-butylamine (0.62 mL, 10 eq) was added at 0° C. The solution was stirred 48 h at room temperature, evaporated and the residue was dissolved in ethyl acetate and washed with a saturated aqueous solution of $Na_2CO_3$. The aqueous layer was extracted with ethyl acetate and then the combined organic layers were dried over $Na_2SO_4$, filtered and evaporated. The residue was thoroughly washed with pentane and filtered off to yield expected compound as an orange powder (0.192 g, quantitative yield) m/z (ESI) 307.2 $[M+H]^+$.

$^1$H NMR (300 MHz, $CDCl_3$) δ 8.19; (d, J=2.8 Hz, 1H), 7.99; (dd, J=8.9 and 2.8 Hz, 1H), 6.96; (d, J=8.9 Hz, 1H), 3.68; (s, 2H), 3.09; (t, J=4.6 Hz, 4H), 2.60-2.45; (m, 4H), 2.31; (s, 3H), 1.11; (s, 9H); $^{13}$C NMR (75 MHz, $CDCl_3$) δ 157.1; (C), 142.7; (C), 135.7; (C), 126.0; (CH), 123.3; (CH), 118.7; (CH), 55.3; ($CH_2$), 51.8; ($CH_2$), 50.7; (C), 46.1; ($CH_3$), 42.7; ($CH_2$), 29.1; ($CH_3$).

Step B: 3-[(tert-butylamino)methyl]-4-(4-methylpiperazin-1-yl)aniline

A mixture of $SnCl_2$ (0.364 g, 4 eq), 1.44 mL of HCl 1M and 5 mL of THF was added to a solution of tert-butyl({[2-(4-methylpiperazin-1-yl)-5-nitrophenyl]methyl})amine (0.147 g, 0.48 mmol) in 20 mL of THF. The reaction mixture was refluxed for 3 h and allowed to cool to room temperature. A saturated aqueous solution of $Na_2CO_3$ was added. The aqueous layer was extracted with DCM. The combined organic layers were dried over $Na_2SO_4$, filtered and evaporated. The residue was purified by flash chromatography (DCM/MeOH/$NH_4OH$//85/15/1) to yield expected compound as a brown oil (65 mg, 49% yield).

$^1$H NMR (300 MHz, $CDCl_3$) δ 6.87; (d, J=8.4 Hz, 1H), 6.55; (d, J=2.7 Hz, 1H), 6.43; (dd, J=8.4 and 2.7 Hz, 1H), 3.57; (s, 2H), 2.79; (t, J=4.5 Hz, 4H), 2.44; (br, 4H), 2.24; (s, 3H), 1.09; (s, 9H); $^{13}$C NMR (75 MHz, $CDCl_3$) δ 143.3; (C), 142.8; (C), 136.8; (C), 121.8; (CH), 117.0; (CH), 114.3; (CH), 55.8; ($CH_2$), 53.0; ($CH_2$), 50.7; (C), 46.0; ($CH_3$), 43.6; ($CH_2$), 28.8; ($CH_3$).

Step C: N-{3-[(tert-butylamino)methyl]-4-(4-methylpiperazin-1-yl)phenyl}-7-chloroquinolin-4-amine 3-[(tert-butylamino)methyl]-4-(4-methylpiperazin-1-yl)aniline (60 mg, 0.22 mmol) and 4,7-dichloroquinoline (43 mg, 1 eq) were refluxed overnight in 10 mL of acetonitrile with 0.43 mL of HCl 1M. The reaction mixture was then evaporated and purified by preparative thin-layer chromatography (DCM/MeOH/$NH_4OH$/18/210.1) to yield expected compound as a pale yellow solid (45 mg, 47% yield). m/z (ESI) 438.3 $[M+H]^+$.

$^1$H NMR (300 MHz, MeOH-$d_4$) δ 8.36; (d, J=5.6 Hz, 1H), 8.27; (d, J=9.1 Hz, 1H), 7.85; (d, J=2.1 Hz, 1H), 7.49; (dd,

J=9.1 and 2.1 Hz, 1H), 7.39-7.24; (m, 3H), 6.90; (d, J=5.6 Hz, 1H), 3.82; (s, 2H), 3.02; (t, J=4.7 Hz, 4H), 2.67; (br, 4H), 2.39; (s, 3H), 1.24; (s, 9H); $^{13}$C NMR (75 MHz, MeOH-d$_4$) δ151.5; (CH), 150.4; (C), 149.2; (C), 148.9; (C), 137.2; (C), 136.7; (C), 135.7; (C), 126.8; (CH), 126.1; (CH), 125.6; (CH), 123.8; (CH), 123.7; (CH), 122.2; (CH), 118.4; (C), 101.5; (CH), 55.8; (CH$_2$), 52.7; (CH$_2$), 51.1; (C), 45.3; (CH$_3$), 43.4; (CH$_2$), 27.9; (CH$_3$).

Example 3

Preparation of 7-chloro-N-[4-(4-methylpiperazin-1-yl)-3-(morpholin-4-ylmethyl)phenyl]quinolin-4-amine (compound 57)

Step A:
[5-amino-2-(4-methylpiperazin-1-yl)phenyl]methanol

[2-(4-Methylpiperazin-1-yl)-5-nitrophenyl]methanol prepared in step A of example 1 (1.00 g, 3.98 mmol) was hydrogenated using ammonium formate (2.51 g, 10 eq) and Pd/C (10% Pd, 0.43 mg, 0.1 eq) in 50 mL of EtOH. The mixture was stirred overnight at room temperature and then filtered through a celite pad. The filtrate was evaporated and the residue was dissolved in DCM and washed with an saturated aqueous solution of Na$_2$CO$_3$. The aqueous layer was extracted with DCM. The combined organic layers were dried over Na$_2$SO$_4$, filtered and evaporated to yield expected compound as a pale yellow oil (0.85 g, 97% yield).
$^1$H NMR (300 MHz, MeOH-d$_4$) δ7.00; (d, J=8.4 Hz, 1H), 6.78; (d, J=2.7 Hz, 1H), 6.64; (dd, J=8.7 and 2.7 Hz, 1H), 4.65; (s, 2H), 2.95-2.85; (m, 4H), 2.70-2.50; (m, 4H), 2.34; (s, 3H); $^{13}$C NMR (75 MHz, MeOH-d$_4$) δ144.5; (C), 142.2; (C), 137.1; (C), 121.2; (CH), 115.7; (CH), 115.2; (CH), 61.2; (CH$_2$), 55.8; (CH$_2$), 52.7; (CH$_2$), 45.2; (CH$_3$).

Step B: {5-[(7-chloroquinolin-4-yl)amino]-2-(4-methylpiperazin-1-yl)phenyl}methanol

[5-amino-2-(4-methylpiperazin-1-yl)phenyl]methanol (100 mg, 0.45 mmol) and 4,7-dichloroquinoline (94 mg, 1.1 eq) were refluxed in 1 mL of n-pentanol overnight. The reaction mixture was then evaporated and purified by flash chromatography (DCM/MeOH/NH$_4$OH//8/2/0.1) to yield expected compound as a pale brown solid (143 mg, 83% yield). m/z (ESI) 383.1 [M+H]$^+$;
$^1$H NMR (300 MHz, MeOH-d$_4$) δ8.42-8.34; (m, 2H), 7.89; (d, J=2.0 Hz, 1H), 7.58; (dd, J=9.1 and 2.1 Hz, 1H), 7.55-7.53; (m, 1H), 7.35-7.28; (m, 2H), 6.89; (d, J=6.1 Hz, 1H), 4.78; (s, 2H), 3.20-3.02; (m, 8H), 2.69; (s, 3H); $^{13}$C NMR (75 MHz, MeOH-d$_4$) δ152.1; (C), 149.3; (CH), 148.0; (C), 146.7; (C), 138.3; (C), 137.0; (C), 135.7; (C), 126.4; (CH), 124.9; (CH), 124.8; (CH), 124.2; (CH), 124.1; (CH), 121.1; (CH), 117.9; (C), 101.2; (CH), 59.9; (CH$_2$), 55.0; (CH$_2$), 51.4; (CH$_2$), 44.0; (CH$_3$).

Step C: 7-chloro-N-[4-(4-methylpiperazin-1-yl)-3-(morpholin-4-ylmethyl)phenyl]quinolin-4-amine To {5-[(7-chloroquinolin-4-yl)amino]-2-(4-methylpiperazin-1-yl)phenyl}methanol (0.300 g, 0.78 mmol) in 6 mL of DMF at 0° C. was added thionyl chloride (0.28 mL, 5 eq). The reaction mixture was warmed up to room temperature and stirred for 2 h. The solvent was evaporated. The residue was suspended in 6 mL of DMF and morpholine (1.39 mL, 20 eq) was added at 0° C. The solution was stirred overnight at room temperature, evaporated and the residue was purified by flash chromatography (DCM/MeOH/NH$_4$OH//9/1/0.1) to yield expected compound as a pale yellow solid (238 mg, 67% yield). m/z (ESI) 452.2 [M+H]$^+$;
$^1$H NMR (300 MHz, MeOH-d$_4$) δ8.51; (d, J=5.3 Hz, 1H), 8.00; (d, J=2.0 Hz, 1H), 7.89; (d, J=9.0 Hz, 1H), 7.47-7.38; (m, 2H), 7.23-7.13; (m, 2H), 6.88-6.82; (m, 2H), 3.72-3.65; (m, 4H), 3.57; (s, 4H), 3.07-2.98; (m, 4H), 2.70-2.47; (m, 8H), 2.36; (s, 3H)

Example 4

Preparation of 7-chloro-N-[3-({[2-(dimethylamino)ethyl](methyl)amino}methyl)-4-(4-methylpiperazin-1-yl)phenyl]quinolin-4-amine (compound 58)

To {5-[(7-chloroquinolin-4-yl)amino]-2-(4-methylpiperazin-1-yl)phenyl}methanol prepared in step B of example 3 (0.100 g, 0.26 mmol) in 2 mL of DMF at 0° C. was added thionyl chloride (0.19 mL, 10 eq). The reaction mixture was warmed up to room temperature and stirred for 2 h. The solvent was evaporated. The residue was suspended in 2 mL of THF and N,N,N'-trimethylethylenediamine (0.33 mL, 10 eq) was added at 0° C. The solution was stirred overnight at room temperature, evaporated and the residue was purified by preparative thin-layer chromatography (DCM/MeOH/NH$_4$OH//8/2/0.1). 232 mg of a yellow oil was obtained. The residue was dissolved in a minimum amount of methanol and precipitated with acetone to yield expected compound as a pale yellow solid (80 mg, 66% yield). m/z (MALDI-TOF) 467.3 [M+H]$^+$;
$^1$H NMR (300 MHz, D$_2$O) δ8.58; (d, J=9.1 Hz, 1H), 8.53; (d, J=7.1 Hz, 1H), 8.16; (d, J=2.0 Hz, 1H), 7.88-8.00; (m, 4H), 7.11; (d, J=7.1 Hz, 1H), 4.98; (s, 2H), 4.10-4.20; (m, 2H), 3.83-4.00; (m, 4H), 3.63-3.80; (m, 2H), 3.45-3.60; (m, 4H), 3.42; (s, 6H), 3.24; (s, 3H), 3.07; (s, 3H); $^{13}$C NMR (75 MHz, D$_2$O) δ158.0; (C), 153.9; (C), 145.1; (CH), 142.3; (C), 141.1; (C), 137.2; (C), 134.0; (CH), 132.3; (CH), 130.5; (CH), 127.3; (CH), 126.9; (C), 126.7; (CH), 121.8; (CH), 118.3; (C), 102.8; (CH), 66.3; (CH$_2$), 61.7; (CH$_2$), 56.1; (CH$_2$), 52.2; (CH$_3$), 45.7; (CH$_3$), 44.2; (CH$_2$), 35.9; (CH$_3$).

Example 5

Preparation of 7-Chloro-N-[3-methyl-4-(4-methylpiperazin-1-yl)-5-(pyrrolidin-1-ylmethyl)phenyl]quinolin-4-amine (compound 59)

Step A: 2-[(2-Bromo-3-methyl-5-nitrophenyl)methyl]-2,3-dihydro-1H-isoindole-1,3-dione N-(Hydroxymethyl)phtalimide (2.36 g, 13.3 mmol) was dissolved in 20 mL of triflic acid at 0° C. The mixture was stirred for 20 minutes and then 2-bromo-5-nitrotoluene (2.88 g, 1 eq) was added. This solution was allowed to warm to room temperature and was stirred for 18 h. The mixture was poured slowly into 300 mL of ice-cold water. The aqueous layer was extracted with DCM. The combined organic layers were washed with 100 mL of water, dried over Na$_2$SO$_4$, filtered and evaporated to yield expected compound as a white solid (4.71 g, 94% yield).
$^1$H NMR (300 MHz, CDCl$_3$) δ7.97; (d, 1H, J=2.6 Hz), 7.84; (m, 2H), 7.71; (m, 3H), 4.95; (s, 2H), 2.48; (s, 3H); $^{13}$C NMR (75 MHz, CDCl$_3$) δ167.7; (C), 146.7; (C), 140.9; (C), 137.3; (C), 134.5; (CH), 132.3; (C), 131.7; (C), 124.1; (CH), 123.8; (CH), 119.9; (CH), 42.3; (CH$_2$), 23.8; (CH$_3$).

Step B: (2-Bromo-3-methyl-5-nitrophenyl)methanamine 4.4 mL of hydrazine hydrate was added to 2-[(2-bromo-3-methyl-5-nitrophenyl)methyl]-2,3-dihydro-1H-isoindole-1,3-dione (4.4 g, 11.7 mmol) in 220 mL of acetonitrile. The mixture was stirred under reflux overnight and then was allowed to cool to room temperature. The phtalhydrazide side product was remove by filtration and washed with 100 mL portions of acetonitrile. The combined acetonitrile filtrates were evaporated and the residue was partitioned between water and ethyl acetate. The organic layer was extracted with two 100 mL portions of aqueous HCl 1 M. The combined acidic aqueous layers were basified to pH=10 with solid potassium hydroxide and then extracted with ethyl acetate. The organic layer was dried over $Na_2SO_4$ filtered and evaporated to yield expected compound as an orange solid (2.15 g, 75% yield). m/z (ESI) 245.0 [M+H]$^+$;
$^1$H NMR (300 MHz, CDCl$_3$) δ8.10; (d, 1H, J=2.8 Hz), 7.94; (d, 1H, J=2.6 Hz), 3.96; (s, 2H), 2.47; (s, 3H); $^{13}$C NMR (75 MHz, CDCl$_3$) δ146.8; (C), 144.4; (C), 140.4; (C), 132.9; (C), 123.4; (CH), 120.6; (CH), 47.0; (CH$_2$), 23.8; (CH$_3$).

Step C: tert-Butyl N-[(2-bromo-3-methyl-5-nitrophenyl)methyl]carbamate

Di-tert-butyl dicarbonate (1.51 g, 6.90 mmol) was added to (2-bromo-3-methyl-5-nitrophenyl)methanamine (1.54 g, 1.1 eq) in 60 mL of THF. The mixture was stirred overnight. After evaporation of the solvent, the residue was thoroughly washed with pentane and filtered off to yield expected compound as off-white powder (1.93 g, 89% yield). m/z (ESI) 369.0 [M+Na]$^+$;
$^1$H NMR (300 MHz, CDCl$_3$) δ7.95; (s, 2H), 5.12; (br, 1H, NH), 4.37; (d, 2H, J=6.3 Hz), 2.45; (s, 3H), 1.41; (s, 9H); $^{13}$C NMR (75 MHz, CDCl$_3$) δ155.7; (C), 146.8; (C), 140.5; (C), 140.4; (C), 132.5; (C), 123.7; (CH), 120.4; (CH), 45.2; (CH$_2$), 28.3; (OH$_3$), 23.7; (CH$_3$).

Step D: tert-Butyl N-{[3-methyl-2-(4-methylpiperazin-1-yl)-5-nitrophenyl]methyl}carbamate In a oven-dried flask and under a nitrogen atmosphere, were placed tert-butyl N-[(2-bromo-3-methyl-5-nitrophenyl)methyl]carbamate (150 mg, 0.43 mmol), (+/−) BINAP (14 mg, 0.05 eq), Cs$_2$CO$_3$ (196 mg, 1.4 eq), Pd$_2$dba$_3$ (10 mg, 0.05 eq) and 3 mL of dry 1,4-dioxanne. N-Methylpiperazine (58 µL, 1.2 eq) was added and the mixture was stirred at 90° C. for 16 h. The solution was filtered through a celite pad and evaporated. The residue was purified by flash chromatography on silica gel (DCM/MeOH/NEt$_3$//9/1/0.1) to yield expected compound as a pale brown solid (100 mg, 64% yield). m/z (ESI) 365.2 [M+H]$^+$;
$^1$H NMR (300 MHz, CDCl$_3$) δ7.91; (s, 1H), 7.82; (s, 1H), 5.04; (br, 1H, NH), 4.34; (d, 2H, J=6.1 Hz), 3.26; (br, 2H), 2.90; (br, 2H), 2.61; (br, 2H), 2.34-2.29; (m, 8H), 1.40; (s, 9H); $^{13}$C NMR (75 MHz, CDCl$_3$) δ156.0; (C), 153.5; (C), 144.6; (C), 139.1; (C), 137.9; (C), 125.6; (CH), 120.5; (CH), 55.8; (CH$_2$), 49.6; (CH$_2$), 46.4; (CH$_3$), 41.5; (CH$_2$), 28.3; (CH$_3$), 20.1; (CH$_3$).

Step E: [3-Methyl-2-(4-methylpiperazin-1-yl)-5-nitrophenyl]methanamine 1.2 mL of acetyl chloride was slowly added to 10 mL of MeOH at 0° C. The solution was stirred for 30 min at room temperature and then tert-butyl N-{[3-methyl-2-(4-methylpiperazin-1-yl)-5-nitrophenyl]methyl}carbamate (300 mg, 0.82 mmol) dissolved in 5 mL of MeOH was added. The reaction mixture was stirred for 2 h and then evaporated. The residue was dissolved in 15 mL of water and washed with diethyl ether. The aqueous layer was made alkaline (pH=10) with an aqueous NaOH 1M and extracted with DCM. The combined organic layers were dried over Na$_2$SO$_4$, filtered and evaporated to yield expected compound as a pale yellow oil (216 mg, quantitative yield). m/z (ESI) 265.2 [M+H]$^+$;
$^1$H NMR (300 MHz, CDCl$_3$) δ8.05; (d, J=2.9 Hz, 1H), 7.85; (d, J=2.8 Hz, 1H), 3.89; (s, 2H), 3.40-2.80; (m, 4H), 2.70-2.30; (m, 4H), 2.37; (s, 3H), 2.32; (s, 3H); $^{13}$C NMR (75 MHz, CDCl$_3$) δ153.9; (C), 144.6; (C), 143.1; (C), 137.9; (C), 125.2; (CH), 121.3; (CH), 55.9; (CH$_2$), 49.8; (CH$_2$), 46.4; (CH$_3$), 43.4; (CH$_2$), 20.1; (CH$_3$).

Step F: 1-methyl-4-[2-methyl-4-nitro-6-(pyrrolidin-1-ylmethyl)phenyl]piperazine A mixture of [3-methyl-2-(4-methylpiperazin-1-yl)-5-nitrophenyl]methanamine (188 mg, 0.71 mmol), 1,4-dibromobutane (93 µL, 1.1 eq) and K$_2$CO$_3$ (490 mg, 5 eq) in 15 mL of acetonitrile was refluxed for 48 h. After filtration and evaporation of the filtrate, the residue was purified by flash chromatography (DCM/MeOH/NH$_4$OH//9/1/0.1) to yield expected compound as a pale yellow oil (120 mg, 53% yield).
$^1$H NMR (300 MHz, CDCl$_3$) δ8.02; (d, J=2.9 Hz, 1H), 7.76; (d, J=2.8 Hz, 1H), 3.58; (s, 2H), 3.10-3.00; (m, 4H), 2.35-2.45; (m, 8H), 2.28; (s, 3H), 2.25; (s, 3H), 1.70-1.60; (m, 4H); $^{13}$C NMR (75 MHz, CDCl$_3$) δ154.5; (C), 143.8; (C), 139.0; (C), 137.3; (C), 125.0; (CH), 123.5; (CH), 57.0; (CH$_2$), 55.8; (CH$_2$), 54.0; (CH$_2$), 49.7; (CH$_2$), 46.7; (CH$_3$), 23.5; (CH$_2$), 20.3; (CH$_3$).

Step G: 3-Methyl-4-(4-methylpiperazin-1-yl)-5-(pyrrolidin-1-ylmethyl)aniline 1-Methyl-4-[2-methyl-4-nitro-6-(pyrrolidin-1-ylmethyl)phenyl]piperazine (90 mg, 0.28 mmol) was hydrogenated using ammonium formate (107 mg, 6 eq) and Pd/C (10% Pd, 15 mg, 0.05 eq) in 2 mL of EtOH. The mixture was stirred overnight at room temperature and then filtered through a celite pad. The filtrate was evaporated and the residue was dissolved in DCM and washed with a saturated aqueous solution of Na$_2$CO$_3$. The aqueous layer was extracted with DCM. The combined organic layers were dried over Na$_2$SO$_4$, filtered and evaporated to yield expected compound as a pale yellow oil (84 mg, quantitative yield).
$^1$H NMR (300 MHz, CDCl$_3$) δ6.65; (d, J=2.8 Hz, 1H), 6.30; (d, J=2.8 Hz, 1H), 3.64; (s, 2H), 3.45; (br, 2H, NH2), 3.20-3.10; (m, 2H), 2.95-2.85; (m, 2H), 2.58-2.45; (m, 6H), 2.37-2.27; (m, 2H), 2.28; (s, 3H), 2.20; (s, 3H), 1.77-1.67; (m, 4H).

Step H: 7-Chloro-N-[3-methyl-4-(4-methylpiperazin-1-yl)-5-(pyrrolidin-1-ylmethyl)phenyl]quinolin-4-amine 3-Methyl-4-(4-methylpiperazin-1-yl)-5-(pyrrolidin-1-ylmethyl)aniline (70 mg, 0.24 mmol) and 4,7-dichloroquinoline (50 mg, 1 eq) were refluxed overnight in 5 mL of acetonitrile with 1.25 mL of HCl 1M. The reaction mixture was then evaporated and purified by flash chromatography (DCM/MeOH/NH$_4$OH//9/1/0.1) to yield expected compound as a white solid (92 mg, 84% yield). m/z (ESI) 450.1 [M+H]$^+$;
$^1$H NMR (300 MHz, CDCl$_3$) δ8.55; (d, J=5.3 Hz, 1H), 8.03; (d, J=2.1 Hz, 1H), 7.83; (d, J=9.0 Hz, 1H), 7.45; (dd, J=2.1 and 9.0 Hz, 1H), 7.27; (m, 1H), 7.02; (d, J=2.7 Hz, 1H), 6.96; (d, J=5.3 Hz, 1H), 6.57; (br, 1H, NH), 3.76; (s, 2H), 3.30-3.20; (m, 2H), 3.15-3.05; (m, 2H), 2.70-2.55; (m, 6H), 2.52-2.42; (m, 2H), 2.40; (s, 3H), 2.38; (s, 3H), 1.85-1.75; (m, 4H).

Example 6

Preparation of 7-Chloro-N-[3-methyl-4-(4-methylpiperazin-1-yl)-5-(morpholin-4-ylmethyl)phenyl]quinolin-4-amine (compound 60)

Step A: 4-{[3-Methyl-2-(4-methylpiperazin-1-yl)-5-nitrophenyl]methyl}morpholinepiperazine A mixture of [3-methyl-2-(4-methylpiperazin-1-yl)-5-nitrophenyl]methanamine prepared in step E of example 5 (465 mg, 1.80 mmol), bis(2-chloroethyl) ether (240 µL, 1.2 eq), $K_2CO_3$ (1.2 g, 5 eq) and NaI (650 mg, 2.3 eq) in 30 mL of acetonitrile was refluxed for 48 h. After filtration and evaporation of the filtrate, the residue was purified by flash chromatography (DCM/MeOH/$NH_4O$//95/5/1) to yield expected compound as a pale yellow oil (139 mg, 23% yield). m/z (ESI) 335.3 $[M+H]^+$.

$^1$H NMR (300 MHz, $CDCl_3$) δ 8.02; (d, J=2.9 Hz, 1H), 7.76; (d, J=2.8 Hz, 1H), 3.58; (s, 2H), 3.10-3.00; (m, 4H), 2.35-2.45; (m, 8H), 2.28; (s, 3H), 2.25; (s, 3H), 1.70-1.60; (m, 4H); $^{13}$C NMR (75 MHz, $CDCl_3$) δ 154.5; (C), 143.8; (C), 139.0; (C), 137.3; (C), 125.0; (CH), 123.5; (CH), 57.0; ($CH_2$), 55.8; ($CH_2$), 54.0; ($CH_2$), 49.7; ($CH_2$), 46.7; ($CH_3$), 23.5; ($CH_2$), 20.3; ($CH_3$).

Step B: 3-Methyl-4-(4-methylpiperazin-1-yl)-5-(morpholin-4-ylmethyl)aniline

4-{[3-Methyl-2-(4-methylpiperazin-1-yl)-5-nitrophenyl]methyl}morpholine-piperazine (113 mg, 0.34 mmol) was hydrogenated using ammonium formate (213 mg, 10 eq) and Pd/C (10% Pd, 36 mg, 0.05 eq) in 5 mL of EtOH. The mixture was stirred overnight at room temperature and then filtered through a celite pad. The filtrate was evaporated and the residue was dissolved in DCM and washed with a saturated aqueous solution of $Na_2CO_3$. The aqueous layer was extracted with DCM. The combined organic layers were dried over $Na_2SO_4$, filtered and evaporated to yield expected compound as a pale yellow oil (92 mg, 89% yield).

$^1$H NMR (300 MHz, $CDCl_3$) δ 6.61; (d, J=2.8 Hz, 1H), 6.37; (d, J=2.8 Hz, 1H), 3.64-3.75; (m, 4H), 3.49; (s, 3H), 3.16-3.26; (m, 2H), 2.90-3.00; (m, 2H), 2.55-2.65; (m, 2H), 2.30-2.50; (m, 6H), 2.34; (s, 3H), 2.25; (s, 3H); $^{13}$C NMR (75 MHz, $CDCl_3$) δ 143.7; (C), 140.4; (C), 138.7; (C), 138.3; (C), 117.0; (CH), 114.7; (CH), 67.3; ($CH_2$), 59.8; ($CH_2$), 56.5; ($CH_2$), 54.0; ($CH_2$), 50.3; ($CH_2$), 46.8; ($CH_3$), 19.9; ($CH_3$).

Step C: 7-Chloro-N-[3-methyl-4-(4-methylpiperazin-1-yl)-5-(morpholin-4-ylmethyl)phenyl]quinolin-4-amine 3-Methyl-4-(4-methylpiperazin-1-yl)-5-(morpholin-4-ylmethyl)aniline (79 mg, 0.26 mmol) and 4,7-dichloroquinoline (56 mg, 1.1 eq) were refluxed overnight in 5 mL of acetonitrile with 0.78 mL of HCl 1M. The reaction mixture was then evaporated and purified by flash chromatography (DCM/MeOH/$NH_4OH$//9/1/0.1) to yield expected compound as a pale yellow solid (75 mg, 62% yield). m/z (ESI) 466.4 $[M+H]^+$.

$^1$H NMR (300 MHz, MeOH-$d_4$) δ 8.33; (d, J=5.6 Hz, 1H), 8.24; (d, J=9.0 Hz, 1H), 7.83; (d, J=2.1 Hz, 1H), 7.46; (dd, J=2.2 and 9.1 Hz, 1H), 7.25; (d, J=2.6 Hz, 1H), 7.06; (d, J=2.5 Hz, 1H), 6.85; (d, J=5.6 Hz, 1H), 3.75-3.62; (m, 4H), 3.58; (s, 2H), 3.32-3.20; (m, 2H), 3.17-3.02; (m, 2H), 2.75-2.62; (m, 2H), 2.58-2.40; (m, 6H), 2.38; (s, 3H), 2.37; (s, 3H); $^{13}$C NMR (75 MHz, MeOH-$d_4$) δ 151.2; (CH), 150.2; (C), 149.1; (C), 145.9; (C), 139.0; (C), 138.2; (C), 136.8; (C), 135.6; (C), 126.7; (CH), 125.5; (CH), 125.5; (CH), 123.6; (CH), 123.5; (CH), 118.4; (C), 101.5; (CH), 67.0; ($CH_2$), 59.8; ($CH_2$), 56.1; ($CH_2$), 53.9; ($CH_2$), 49.5; ($CH_2$), 45.5; ($CH_3$), 19.0; ($CH_3$).

Example 7

7-Chloro-N-[3-methyl-4-(morpholin-4-yl)-5-(pyrrolidin-1-ylmethyl)phenyl]quinolin-4-amine (compound 61)

Step A: tert-Butyl N-{[3-methyl-2-(morpholin-4-yl)-5-nitrophenyl]methyl}carbamate In a oven-dried flask and under a nitrogen atmosphere, were placed tert-butyl N-[(2-bromo-3-methyl-5-nitrophenyl)methyl]carbamate prepared in step C of example 5 (500 mg, 1.45 mmol), (+/−) BINAP (45 mg, 0.07 mmol), $Cs_2CO_3$ (661 mg, 2.03 mmol), $Pd_2dba_3$ (33 mg, 0.07 eq) and 10 mL of dry 1,4-dioxanne. Morpholine (152 µL, 1.74 mmol) was added and the mixture was stirred at 90° C. for 24 h. The solution was filtered through a celite pad and evaporated. The residue was purified by flash chromatography on silica gel (DCM/AcOEt//9/1) to yield expected compound as a pale brown solid (360 mg, 71% yield); m/z (ESI) 352.2 $[M+H]^+$.

$^1$H NMR (300 MHz, $CDCl_3$) δ 8.00; (d, 1H, J=2.1 Hz), 7.92; (d, 1H, J=2.7 Hz), 5.05; (br, 1H, NH), 4.46; (d, 2H, J=6.0 Hz), 3.83; (br, 4H), 3.50-2.70; (m, 4H), 2.45; (s, 3H), 1.46; (s, 9H); $^{13}$C NMR (75 MHz, $CDCl_3$) δ 156.5; (C), 153.5; (C), 145.4; (C), 139.8; (C), 138.6; (C), 126.3; (CH), 121.3; (CH), 68.3; ($CH_2$), 50.6; ($CH_2$), 42.1; ($CH_2$), 29.0; ($CH_3$), 20.7; ($CH_3$).

Step B: [3-Methyl-2-(morpholin-4-yl)-5-nitrophenyl]methanamine hydrochloride 0.81 mL of acetyl chloride was slowly added to 5 mL of MeOH at 0° C. The solution was stirred for 30 min at room temperature and then tert-butyl N-{[3-methyl-2-(morpholin-4-yl)-5-nitrophenyl]methyl}carbamate (200 mg, 0.57 mmol) dissolved in 5 mL of MeOH was added. The reaction mixture was stirred for 3 h and then evaporated to yield expected compound as an orange solid (162 mg, 99% yield).

Step C: 4-[2-Methyl-4-nitro-6-(pyrrolidin-1-ylmethyl)phenyl]morpholine

A mixture of [3-Methyl-2-(morpholin-4-yl)-5-nitrophenyl]methanamine hydrochloride (160 mg, 0.56 mmol), 1,4-dibromobutane (80 µL, 0.67 mmol) and $K_2CO_3$ (542 mg, 3.92 mmol) in 10 mL of acetonitrile was heated at 60° C. for 48 h. After filtration and evaporation of the filtrate, the residue was purified by flash chromatography (DCM/MeOH/$NH_4OH$//9/1/0.1) to yield expected compound as a pale yellow oil (100 mg, 58% yield); m/z (ESI) 306.3 $[M+H]^+$.

$^1$H NMR (300 MHz, MeOH-$d_4$) δ 8.16; (d, J=3.0 Hz, 1H), 7.98; (d, J=2.7 Hz, 1H), 3.90-3.78; (m, 6H), 3.20; (br, 4H), 2.65-2.52; (m, 4H), 2.48; (s, 3H), 1.90-1.80; (m, 4H); $^{13}$C NMR (75 MHz, MeOH-$d_4$) δ 154.5; (C), 144.6; (C), 139.2;

(C), 138.4; (C), 125.0; (CH), 123.3; (CH), 67.8; (CH$_2$), 57.0; (CH$_2$), 54.1; (CH$_2$), 50.4; (CH$_2$), 23.4; (CH$_2$), 19.3; (CH$_3$).

Step D: 3-Methyl-4-(morpholin-4-yl)-5-(pyrrolidin-1-ylmethyl)aniline

4-[2-Methyl-4-nitro-6-(pyrrolidin-1-ylmethyl)phenyl]morpholine (62 mg, 0.20 mmol) was hydrogenated using ammonium formate (128 mg, 2.00 mmol) and Pd/C (10% Pd, 21 mg, 0.02 mmol) in 2 mL of EtOH. The mixture was stirred overnight at room temperature and then filtered through a celite pad. The filtrate was evaporated and the residue was dissolved in DCM and washed with a saturated aqueous solution of Na$_2$CO$_3$. The aqueous layer was extracted with DCM. The combined organic layers were dried over Na$_2$SO$_4$, filtered and evaporated to yield expected compound as a pale yellow oil (55 mg, 99% yield); m/z (ESI) 276.3 [M+H]$^+$.

Step E: 7-Chloro-N-[3-methyl-4-(morpholin-4-yl)-5-(pyrrolidin-1-ylmethyl) phenyl]quinolin-4-amine 3-Methyl-4-(morpholin-4-yl)-5-(pyrrolidin-1-ylmethyl)aniline (46 mg, 0.17 mmol) and 4,7-dichloroquinoline (40 mg, 0.20 mmol) were refluxed overnight in 5 mL of acetonitrile with 0.51 mL of HCl 1M. The reaction mixture was then evaporated and purified by flash chromatography (DCM/MeOH/NH$_4$OH//95/5/0 to 90/10/1) to yield expected compound as a white solid (53 mg, 71% yield); m/z (ESI) 437.3 [M+H]$^+$;
$^1$H NMR (300 MHz, CDCl$_3$) δ8.43; (d, J=5.5 Hz, 1H), 8.24; (d, J=9.0 Hz, 1H), 7.90; (d, J=1.9 Hz, 1H), 7.55; (d, J=2.1 Hz, 1H), 7.30; (dd, J=1.9 and 9.0 Hz, 1H), 7.15; (d, J=2.0 Hz, 1H), 6.89; (d, J=5.5 Hz, 1H), 4.15; (s, 1H), 3.89; (d, J=10.9 Hz, 2H), 3.69; (t, J=9.2 Hz, 2H), 3.38; (t, J=9.4 Hz, 2H), 3.01; (br, 4H), 2.74; (d, J=12.0 Hz, 2H), 2.37; (s, 3H), 1.98; (br, 4H); $^{13}$C NMR (75 MHz, CDCl$_3$) δ151.0; (CH), 148.8; (C), 148.7; (C), 144.3; (C), 138.8; (C), 137.9; (C), 135.8; (C), 134.4; (C), 127.6; (CH), 126.1; (CH), 125.8; (CH), 123.6; (CH), 122.6; (CH), 118.5; (C), 102.5; (CH), 68.2; (CH$_2$), 55.1; (CH$_2$), 54.3; (CH$_2$), 50.8; (CH$_2$), 23.7; (CH$_2$), 20.5; (CH$_3$).

Example 8

Preparation of 5-[(7-Chloroquinolin-4-yl)amino]-1-N,3-N-bis[3-(4-methylpiperazin-1-yl)propyl]benzene-1,3-dicarboxamide (compound 62)

Step A: 1,3-Dimethyl 5-[(7-chloroquinolin-4-yl)amino]benzene-1,3-dicarboxylate 1,3-dimethyl 5-aminobenzene-1,3-dicarboxylate (2.09 g, 10 mmol) and 4,7-dichloroquinoline (1.98 g, 1 eq) were refluxed in 200 mL of ethanol for 3 h. The reaction mixture was then cooled to room temperature and the precipitate was removed by filtration and washed successively with a saturated aqueous solution of NaHCO$_3$, water, ethanol and then petroleum ether to yield expected compound as a yellow powder (2.90 g, 78% yield). m/z (ESI) 371.0 [M+H]$^+$.
$^1$H NMR (300 MHz, CDCl$_3$) δ8.37; (s, 1H), 8.29; (d, J=9.0 Hz, 1H), 8.07; (d, J=6.9 Hz, 1H), 7.99-7.97; (m, 2H), 7.72-7.70; (m, 1H), 7.46; (d, J=9.3 Hz, 1H), 6.59; (d, J=6.9 Hz, 1H), 3.67; (s, 6H).

Step B: 5-[(7-Chloroquinolin-4-yl)amino]-1-N,3-N-bis[3-(4-methylpiperazin-1-yl)propyl]benzene-1,3-dicarboxamide Synthesized from 1,3-dimethyl 5-[(7-chloroquinolin-4-yl)amino]benzene-1,3-dicarboxylate (0.2 g, 0.54 mmol) according to general procedure A (reflux for 24 h) with 2 eq of AlMe$_3$ and amine in 5 mL of DCM. The residue was purified by preparative thin-layer chromatography (acetone/NH$_4$OH//9/1) to yield expected compound (334 mg, 51%) as a brown oil. m/z (ESI) 621.2 [M+H]$^+$.
$^1$H NMR (300 MHz, MeOH-d$_4$) δ8.31; (d, J=5.5 Hz, 1H), 8.20; (d, J=9.1 Hz, 1H), 7.99-7.95; (m, 1H), 7.90-7.84; (m, 2H), 7.74; (d, J=2.0 Hz, 1H), 7.37; (dd, J=9.0 and 2.0 Hz, 1H), 6.95; (d, J=5.5 Hz, 1H), 3.45-3.30; (m, 4H), 2.70-2.21; (m, 20H), 2.15; (s, 6H), 1.80-1.60; (m, 4H); $^{13}$C NMR (75 MHz, MeOH-d$_4$) δ167.6; (C), 151.8; (CH), 149.3; (C), 149.1; (C), 141.4; (C), 136.8; (C), 136.0; (CH), 127.1; (CH), 126.2; (CH), 124.1; (CH), 124.0; (CH), 121.8; (CH), 119.0; (C), 102.7; (CH), 56.4; (CH$_2$), 54.7; (CH$_2$), 52.7; (CH$_2$), 45.0; (CH$_3$), 38.9; (CH$_2$), 26.2; (CH$_2$).

Another fraction give methyl 3-[(7-chloroquinolin-4-yl)amino]-5-[(4-methylpiperazin-1-yl)carbonyl]benzoate (example 67) (31 mg, 12%) as a yellow powder.

Example 9

Preparation of N-{3,5-Bis[(4-methylpiperazin-1-yl)carbonyl]phenyl}-7-chloroquinolin-4-amine (compound 63)

Synthesized from 1,3-dimethyl 5-[(7-chloroquinolin-4-yl)amino]benzene-1,3-dicarboxylate prepared from step A of example 8 (0.2 g, 0.54 mmol) according to general procedure A (reflux for 24 h) with 1 eq of AlMe$_3$ and amine in 5 mL of DCM. The residue was purified by preparative thin-layer chromatography (acetone/NH$_4$OH//9/1) to yield expected compound (273 mg, 55%) as a yellow oil. m/z (ESI) 507.0 [M+H]$^+$.
$^1$H NMR (300 MHz, MeOH-d$_4$) δ8.53; (d, J=5.5 Hz, 1H), 8.31; (d, J=9.1 Hz, 1H), 7.95; (d, J=2.1 Hz, 1H), 7.58; (dd, J=9.1 and 2.2 Hz, 1H), 7.52; (d, J=1.4 Hz, 2H), 7.25; (t, J=1.4 Hz, 1H), 7.20; (d, J=5.5 Hz, 1H), 3.81; (br, 4H), 3.57; (br, 4H), 2.63-2.40; (m, 8H), 2.36; (s, 6H).

Another fraction give methyl 3-[(7-chloroquinolin-4-yl)amino]-5-[(4-methylpiperazin-1-yl)carbonyl]benzoate (compound 68) (235 mg, 55%) as a yellow oil.

Example 10

Preparation of N-[3,5-Bis({4-[3-(dimethylamino)propyl]piperazin-1-yl}carbonyl)phenyl]-7-chloroquinolin-4-amine (compound 64)

Synthesized from 1,3-dimethyl 5-[(7-chloroquinolin-4-yl)amino]benzene-1,3-dicarboxylate prepared from step A of example 8 (0.3 g, 0.81 mmol) according to general procedure A (reflux for 48 h) with 2.5 eq of AlMe$_3$ and amine in 10 mL of DCM. The residue was purified by preparative thin-layer chromatography (acetone/NH$_4$OH//9/1) to yield expected compound (12 mg, 2%) as a yellow oil. m/z (MALDI-TOF) 649.4 [M+H]$^+$.
$^1$H NMR (300 MHz, MeOH-d$_4$) δ8.52; (d, J=5.5 Hz, 1H), 8.30; (d, J=9.1 Hz, 1H), 7.93; (d, J=2.1 Hz, 1H), 7.57; (dd, J=9.1 and 2.1 Hz, 1H), 7.51; (d, J=1.3 Hz, 2H), 7.23; (t, J=1.3 Hz, 1H), 7.19; (d, J=5.5 Hz, 1H), 3.81; (br, 4H), 3.56; (br, 4H), 2.65-2.35; (m, 16H), 2.28; (s, 12H), 1.80-1.65; (m, 4H); $^{13}$C NMR (75 MHz, MeOH-d$_4$) δ169.7; (C), 151.7; (CH), 149.7; (C), 148.9; (C), 141.8; (C), 137.7; (C), 136.1; (C), 127.1; (CH), 126.3; (CH), 123.8; (CH), 121.6; (CH), 120.6; (CH), 119.2; (C), 103.2; (CH), 57.5; (CH$_2$), 56.2; (CH$_2$), 48.0; (CH$_2$), 44.4; (CH$_3$), 42.2; (CH$_2$), 24.3; (CH$_2$).

Another fraction give methyl 3-[(7-chloroquinolin-4-yl)amino]-5-({4-[3-(dimethylamino)propyl]piperazin-1-yl}carbonyl)benzoate (compound 69) (53 mg, 13%) as a yellow oil.

Example 11

Preparation of N-[3,5-Bis(pyrrolidin-1-ylmethyl)phenyl]-7-chloroquinolin-4-amine (compound 65)

Step A: 3,5-Bis[(pyrrolidin-1-yl)carbonyl]aniline

A solution of $AlMe_3$ (2M in toluene, 19.5 mL, 2 eq) was added dropwise to a solution of pyrrolidine (3.25 mL, 2 eq) in 50 mL of anhydrous DCM at 0° C. The reaction mixture was allowed to warm up to room temperature and stirred for 1 h. 1,3-Dimethyl 5-aminobenzene-1,3-dicarboxylate (4.10 g, 19.5 mmol) was added and the reaction mixture was refluxed for 38 h. The mixture was then poured in ice cooled water and filtered. The aqueous filtrate was extracted with $CHCl_3$. The combined organic layers were dried over $MgSO_4$, filtered and evaporated to give 3.5 g of expected compound which was used in the next step without further purification.

Step B: N-{3,5-Bis[(pyrrolidin-1-yl)carbonyl]phenyl}-7-chloroquinolin-4-amine 3,5-Bis[(pyrrolidin-1-yl)carbonyl]aniline (287 mg, 1.0 mmol) and 4,7-dichloroquinoline (198 mg, 1 eq) were refluxed in 20 mL of ethanol and 2 mL of HCl 1M for 12 h. The reaction mixture was then evaporated. The residue was purified by flash chromatography (DCM/MeOH//9/1) to yield expected compound as a yellow powder (2.90 g, 78% yield). m/z (ESI) 449.1 $[M+H]^+$.
$^1H$ NMR (300 MHz, $CDCl_3$) δ11.50; (br, 1H), 9.08; (d, J=9.0 Hz, 1H), 8.30-8.10; (m, 2H), 7.85-7.75; (m, 2H), 7.68-7.60; (m, 1H), 7.44; (d, J=8.4 Hz, 1H), 6.93-6.82; (m, 1H), 3.70-3.48; (m, 8H), 2.03-1.85; (m, 8H); $^{13}C$ NMR (75 MHz, $CDCl_3$) δ167.7; (C), 155.2; (C), 142.3; (CH), 140.5; (C), 139.1; (C), 138.7; (C), 137.6; (C), 128.3; (CH), 126.8; (CH), 125.3; (CH), 124.8; (CH), 119.6; (CH), 116.4; (C), 100.5; (CH), 50.0; ($CH_2$), 46.9; ($CH_2$), 26.6; ($CH_2$), 24.5; ($CH_2$).

Step C: N-[3,5-Bis(pyrrolidin-1-ylmethyl)phenyl]-7-chloroquinolin-4-amine

To a suspension of N-{3,5-bis[(pyrrolidin-1-yl)carbonyl]phenyl}-7-chloroquinolin-4-amine (84 mg, 0.19 mmol) in 15 mL of anhydrous THF, was added portionwise $LiAlH_4$ (71 mg, 10 eq). The reaction mixture was stirred at room temperature for 2 h and then 10 mL of ethyl acetate was added. The mixture was filtered through a celite pad. The filtrate was evaporated and the residue was purified by preparative thin-layer chromatography (DCM/MeOH/$NH_4OH$//95/5/1) to yield expected compound (4 mg, 5%) as a yellow oil. m/z (ESI) 420.9 $[M+H]^+$.
$^1H$ NMR (300 MHz, $CDCl_3$) δ8.56; (d, J=5.3 Hz, 1H), 8.01; (d, J=2.1 Hz, 1H), 7.89; (d, J=9.0 Hz, 1H), 7.44; (dd, J=8.9 and 2.1 Hz, 1H), 7.30-7.22; (m, 2H), 7.14-7.10; (m, 1H), 7.03-6.80; (m, 2H), 2.70-2.55; (m, 8H), 1.90-1.78; (m, 8H).

Example 12

Preparation of 4-[(7-Chloroquinolin-4-yl)amino]-2,6-bis (pyrrolidin-1-ylmethyl)phenol (compound 66)

Step A: 4-[(7-Chloroquinolin-4-yl)amino]phenol

4-Aminophenol (1.09 g, 10 mmol) and 4,7-dichloroquinoline (1.98 g, 1 eq) were refluxed in 50 mL of ethanol for 2 h. The reaction mixture was then cooled to room temperature and the precipitate was removed by filtration and washed successively with a saturated aqueous solution of $NaHCO_3$, water, methanol and then petroleum ether to yield expected compound as a yellow powder (2.57 g, 95% yield). m/z (ESI) 271.1 $[M+H]^+$.
$^1H$ NMR (300 MHz, DMSO-$d_6$) δ10.7; (br, 1H), 9.88; (br, 1H), 8.77; (d, J=9.1 Hz, 1H), 8.43; (d, J=6.8 Hz, 1H), 8.09; (d, J=2.1 Hz, 1H), 7.77; (dd, J=9.1 and 2.1 Hz, 1H), 7.23; (d, J=8.8 Hz, 1H), 6.94; (d, J=8.8 Hz, 1H), 6.60; (d, J=6.8 Hz, 1H).

Step B: 4-[(7-Chloroquinolin-4-yl)amino]-2,6-bis (pyrrolidin-1-ylmethyl)phenol

4-[(7-Chloroquinolin-4-yl)amino]phenol (2.45 g, 9 mmol), pyrrolidine (3.25 mL, 4.4 eq) and a 37% aqueous solution of formaldehyde (3 mL, 4.4 eq) were stirred at room temperature for 18 h in 5 mL of ethanol. The reaction mixture was then evaporated and the residue was purified by flash chromatography (DCM/MeOH/$NH_4OH$/8:2:0.1) to yield expected compound as a brown solid (2.90 g, 74% yield). m/z (ESI) 437.1 $[M+H]^+$.
$^1H$ NMR (300 MHz, DMSO-$d_6$) δ8.91; (br, 1H), 8.41; (d, J=9.0 Hz, 1H), 8.36; (d, J=5.4 Hz, 1H), 7.84; (d, J=2.1 Hz, 1H), 7.51; (dd, J=9.0 and 2.1 Hz, 1H), 7.06; (s, 2H), 6.60; (d, J=5.4 Hz, 1H), 2.68-2.52; (m, 8H), 1.83-1.60; (m, 8H).

Example 13

Preparation of Methyl 3-[(7-chloroquinolin-4-yl)amino]-5-[(4-methylpiperazin-1-yl)carbonyl]benzoate (compound 67)

Prepared as described in step B of example 8.
m/z (ESI) 496.0 $[M+H]^+$.
$^1H$ NMR (300 MHz, MeOH-$d_4$) δ8.47; (d, J=5.5 Hz, 1H), 8.30; (d, J=9.1 Hz, 1H), 8.26-8.20; (m, 1H), 8.18-8.12; (m, 1H), 8.10-8.03; (m, 1H), 7.90; (d, J=1.4 Hz, 1H), 7.54; (dd, J=9.0 and 1.4 Hz, 1H), 7.08; (d, J=5.5 Hz, 1H), 3.96; (s, 3H), 3.46; (t, J=6.8 Hz, 2H), 2.60-2.40; (m, 10H), 2.27; (s, 3H), 1.84; (q, J=7.1 Hz, 2H); $^{13}C$ NMR (75 MHz, MeOH-$d_4$) δ167.4; (C), 166.3; (C), 151.5; (CH), 149.1; (C), 149.0; (C), 141.5; (C), 136.6; (C), 136.0; (C), 132.1; (C), 126.8; (CH), 126.2; (CH), 125.8; (CH), 125.5; (CH), 124.0; (CH), 123.5; (CH), 118.9; (C), 102.5; (CH), 55.9; ($CH_2$), 54.2; ($CH_2$), 52.1; ($CH_3$), 51.9; ($CH_2$), 44.2; ($CH_3$), 38.6; ($CH_2$), 25.9; ($CH_2$).

Example 14

Preparation of Methyl 3-[(7-chloroquinolin-4-yl)amino]-5-[(4-methylpiperazin-1-yl)carbonyl]benzoate (compound 68)

Prepared as described in example 9.
m/z (ESI) 439.0 $[M+H]^+$.
$^1H$ NMR (300 MHz, MeOH-$d_4$) δ8.53; (d, J=5.5 Hz, 1H), 8.32; (d, J=9.1 Hz, 1H), 8.14-8.12; (m, 1H), 7.95; (d, J=2.0 Hz, 1H), 7.84-7.82; (m, 1H), 7.67-7.65; (m, 1H), 7.58; (dd, J=9.1 and 2.2 Hz, 1H), 7.15; (d, J=5.5 Hz, 1H), 3.97; (s, 3H), 3.83; (br, 2H), 3.57; (br, 2H), 2.62-2.40; (m, 4H), 2.37; (s, 3H).

Example 15

Preparation of Methyl 3-[(7-chloroquinolin-4-yl) amino]-5-({4-[3-(dimethylamino)propyl]piperazin-1-yl}carbonyl)benzoate (compound 69)

Prepared as described in example 10.
m/z (MALDI-TOF) 510.3 [M+H]$^+$.
$^1$H NMR (300 MHz, MeOH-d$_4$) δ8.45; (d, J=5.5 Hz, 1H), 8.24; (d, J=9.1 Hz, 1H), 8.06-8.03; (m, 1H), 7.88; (d, J=2.1 Hz, 1H), 7.78-7.75; (m, 1H), 7.62-7.59; (m, 1H), 7.50; (dd, J=9.1 and 2.2 Hz, 1H), 7.08; (d, J=5.5 Hz, 1H), 3.93; (s, 3H), 3.79; (br, 2H), 3.52; (br, 2H), 2.60-2.30; (m, 8H), 2.24; (s, 6H), 1.78-1.62; (m, 2H).

Example 16

Preparation of N-[3,5-bis(4-methylpiperazin-1-yl)phenyl]-7-chloroquinolin-4-amine (compound 70)

Step A: 2,6-Dibromo-4-nitroaniline 2,6-Dibromo-4-nitroaniline was prepared from p-nitroaniline as described by Shepherd, R. G. J. *Org. Chem.* 1947, 12, 275.

Step B: 3,5-Dibromonitrobenzene

NaNO$_2$ (4.1 g, 59.1 mmol) was added portionwise to a solution of 2,6-dibromo-4-nitroaniline (5 g, 3.5 eq) in 20% H$_2$SO$_4$ and AcOEt (each 40 mL) at a rate to keep the internal temperature at 50-55° C. After heating for an additional 10 min, the mixture was cooled, diluted, and extracted with AcOEt. The combined organic layers were dried over Na$_2$SO$_4$, filtered and evaporated. The residue was purified by flash chromatography (cyclohexane/DCM//7/3 then 8/2) to yield expected compound as a white solid (1.94 g, 41% yield).
$^1$H NMR (300 MHz, CDCl$_3$) δ8.32; (d, J=1.8 Hz, 2H), 8.00; (t, J=1.8 Hz, 1H).

Step C: 1-methyl-4-[3-(4-methylpiperazin-1-yl)-5-nitrophenyl]piperazine

In a oven-dried flask and under a nitrogen atmosphere, were placed 3,5-dibromonitrobenzene (500 mg, 1.78 mmol), (+/−) BINAP (110 mg, 0.1 eq), Cs$_2$CO$_3$ (1.62 g, 3 eq), Pd$_2$dba$_3$ (81 mg, 0.11 eq) and 10 mL of dry 1,4-dioxane. N-Methylpiperazine (0.47 mL, 2.4 eq) was added and the mixture was stirred at 90° C. for 48 h. The solution was filtered through a celite pad and evaporated. The residue was purified by flash chromatography on silica gel (DCM/MeOH/NH$_4$OH//95/5/1) to yield expected compound as an orange solid (258 mg, 45% yield). m/z (MALDI-TOF) 320.2 [M+H]$^+$;
$^1$H NMR (300 MHz, CDCl$_3$) δ7.17; (d, J=2.1 Hz, 2H), 6.59; (t, J=2.1 Hz, 1H), 3.20; (t, J=4.8 Hz, 8H), 2.51; (t, J=5.1 Hz, 8H), 2.29; (s, 6H); $^{13}$C NMR (75 MHz, CDCl$_3$) δ152.4; (C), 150.1; (C), 108.1; (CH), 101.8; (CH), 54.8; (CH$_2$), 48.7; (CH$_2$), 46.1; (CH$_3$).

Step D: 3,5-bis(4-methylpiperazin-1-yl)aniline 1-methyl-4-[3-(4-methylpiperazin-1-yl)-5-nitrophenyl]piperazine (258 mg, 0.81 mmol) was hydrogenated using ammonium formate (0.51 g, 10 eq) and Pd/C (10% Pd, 85 mg, 0.1 eq) in 8 mL of EtOH. The mixture was stirred overnight at room temperature and then filtered through a celite pad. The filtrate was evaporated and the residue was dissolved in DCM and washed with a saturated aqueous solution of Na$_2$CO$_3$. The aqueous layer was extracted with DCM. The combined organic layers were dried over Na$_2$SO$_4$, filtered and evaporated to yield expected compound as a brown powder (212 mg, 90% yield). m/z (MALDI-TOF) 290.2 [M+H]$^+$.
$^1$H NMR (300 MHz, CDCl$_3$) δ5.97; (t, J=1.8 Hz, 1H), 5.84; (d, J=2.1 Hz, 2H), 3.17; (t, J=4.8 Hz, 8H), 2.54; (t, J=5.1 Hz, 8H), 2.34; (s, 6H); $^{13}$C NMR (75 MHz, CDCl$_3$) δ153.6; (C), 148.1; (C), 96.4; (CH), 96.2; (CH), (CH$_2$ (CH$_2$), 46.5; (CH$_3$).

Step E: N-[3,5-bis(4-methylpiperazin-1-yl)phenyl]-7-chloroquinolin-4-amine

In a oven-dried flask and under a nitrogen atmosphere, were placed 3,5-bis(4-methylpiperazin-1-yl)aniline (148 mg, 0.51 mmol), 4,7-dichloroquinoline (101 mg, 1 eq), (+/−) BINAP (16 mg, 0.05 eq), Cs$_2$CO$_3$ (232 mg, 1.4 eq), Pd$_2$dba$_3$ (12 mg, 0.02 eq) and 2 mL of dry 1,4-dioxane. The mixture was stirred at 90° C. for 48 hours. The solution was filtered through a celite pad and evaporated. The residue was purified by flash chromatography on silica gel (DCM/MeOH/NH$_4$OH//8/2/0 then 8/2/0.1). 221 mg of an yellow solid was obtained. A subsequent purification by preparative thin-layer chromatography (DCM/MeOH/NH$_4$OH//8/2/0.1) yield expected compound as a yellow solid (65 mg, 28% yield). m/z (ESI) 451.2 [M+H]$^+$;
$^1$H NMR (300 MHz, CDCl$_3$) δ8.53; (d, J=5.4 Hz, 1H), 8.03; (d, J=2.1 Hz, 1H), 7.84; (d, J=8.7 Hz, 1H), 7.44; (dd, J=9.0 and 2.1 Hz, 1H), 6.99; (d, J=5.4 Hz, 1H), 6.60; (br, 1H), 6.35-6.40; (m, 2H), 6.30-6.35; (m, 1H), 3.24; (t, J=5.1 Hz, 8H), 2.60; (t, J=5.1 Hz, 8H), 2.37; (s, 6H); $^{13}$C NMR (75 MHz, CDCl$_3$) δ153.5; (C), 151.7; (CH), 149.4; (C), 148.8; (C), 141.0; (C), 135.6; (C), 128.5; (CH), 126.1; (CH), 122.1; (CH), 118.3; (C), 103.0; (CH), 101.2; (CH), 55.3; (CH$_2$), 49.3; (CH$_2$), 46.3; (CH$_3$).

Example 17

Preparation of N-[3,5-bis(morpholin-4-yl)phenyl]-7-chloro-quinolin-4-amine (compound 71)

Step A: 4-[3-(morpholin-4-yl)-5-nitrophenyl]morpholine

In a oven-dried flask and under a nitrogen atmosphere, were placed 3,5-dibromonitrobenzene prepared from step B of example 16 (150 mg, 0.53 mmol), (+/−) BINAP (33 mg, 0.1 eq), Cs$_2$CO$_3$ (0.49 g, 3 eq), Pd$_2$dba$_3$ (24 mg, 0.05 eq) and 3 mL of dry 1,4-dioxane. Morpholine (0.11 mL, 2.4 eq) was added and the mixture was stirred at 90° C. for 5 days. The solution was filtered through a celite pad and evaporated. The residue was purified by flash chromatography on silica gel (DCM/MeOH/NH$_4$OH//98/2/1) to yield expected compound as an orange solid (123 mg, 51% yield). m/z (MALDI-TOF) 294.1 [M+H]$^+$;
$^1$H NMR (300 MHz, CDCl$_3$) δ7.26; (s, 2H), 6.65; (s, 1H), 3.87; (t, J=4.8 Hz, 8H), 3.22; (t, J=4.8 Hz, 8H).

Step B: 3,5-bis(morpholin-4-yl)aniline

4-[3-(morpholin-4-yl)-5-nitrophenyl]morpholine (123 mg, 0.42 mmol) was hydrogenated using ammonium formate (0.26 g, 10 eq) and Pd/C (10% Pd, 45 mg, 0.1 eq) in 4 mL of EtOH. The mixture was stirred overnight at room temperature and then filtered through a celite pad. The filtrate was evaporated and the residue was dissolved in DCM and washed with a saturated aqueous solution of Na$_2$CO$_3$. The aqueous layer was extracted with DCM. The combined organic layers were dried over Na$_2$SO$_4$, filtered and evaporated to yield expected compound as a brown powder (63 mg, 57% yield).

$^1$H NMR (300 MHz, CDCl$_3$) δ5.93; (t, J=1.8 Hz, 1H), 5.84; (d, J=1.8 Hz, 2H), 3.83; (t, J=5.1 Hz, 8H), 3.11; (t, J=5.1 Hz, 8H).

Step C: N-[3,5-bis(morpholin-4-yl)phenyl]-7-chloro-quinolin-4-amine

In a oven-dried flask and under a nitrogen atmosphere, were placed 3,5-bis(morpholin-4-yl)aniline (63 mg, 0.22 mmol), 4,7-dichloroquinoline (43 mg, 1 eq), (+/−) BINAP (7 mg, 0.1 eq), Cs$_2$CO$_3$ (99 mg, 1.4 eq), Pd$_2$dba$_3$ (5 mg, 0.02 eq) and 2 mL of dry 1,4-dioxane. The mixture was stirred at 90° C. for 24 h. The solution was filtered through a celite pad and evaporated. The residue was purified by preparative thin-layer chromatography (DCM/MeOH//95/5) to yield expected compound as a yellow solid (27 mg, 29% yield). m/z (ESI) 425.3 [M+H]$^+$;

$^1$H NMR (300 MHz, MeOH-d$_4$) δ8.35; (d, J=5.7 Hz, 1H), 8.27; (d, J=9.1 Hz, 1H), 7.85; (d, J=2.1 Hz, 1H), 7.49; (dd, J=9.1 and 2.1 Hz, 1H), 6.94; (d, J=5.7 Hz, 1H), 6.47-6.52; (m, 2H), 6.40-6.47; (m, 1H), 3.82; (t, J=4.7 Hz, 8H), 3.15; (t, J=4.9 Hz, 8H); $^{13}$C NMR (75 MHz, MeOH-d$_4$) δ153.9; (C), 150.9; (C), 150.7; (CH), 148.4; (C), 141.1; (C), 136.0; (C), 126.1; (CH), 125.8; (CH), 123.8; (CH), 118.3; (C), 103.7; (CH), 102.0; (CH), 101.1; (CH), 67.0; (CH$_2$), 49.7; (CH$_2$).

Example 18

Preparation of 3-[(7-chloroquinolin-4-yl)amino]-5-(4-methyl-piperazin-1-yl)phenol (compound 72)

3,5-bis(4-methylpiperazin-1-yl)aniline prepared from step D of example 16 (95 mg, 0.33 mmol) and 4,7-dichloroquinoline (65 mg, 1 eq) were refluxed 3 h in 4 mL of acetonitrile with 0.98 mL of HCl 1 M. The reaction mixture was then evaporated and purified by flash chromatography (DCM/MeOH/NH$_4$OH//9/1/0.1) to yield expected compound as a yellow oil (28 mg, 23% yield). m/z (ESI) 369.2 [M+H]$^+$;

$^1$H NMR (300 MHz, MeOH-d$_4$) δ8.32; (d, J=5.6 Hz, 1H), 8.20; (d, J=9.0 Hz, 1H), 7.80; (d, J=2.0 Hz, 1H), 7.42; (dd, J=2.1 and 9.0 Hz, 1H), 6.94; (d, J=5.6 Hz, 1H), 6.40-6.43; (m, 1H), 6.32-6.35; (m, 1H), 6.23-6.26; (m, 1H), 3.15; (t, J=5.1 Hz, 4H), 2.55; (t, J=5.1 Hz, 4H), 2.30; (s, 3H).

Example 19

Preparation of 3-Amino-5-[(7-chloroquinolin-4-yl) amino]benzonitrile hydrochloride (compound 73)

Step A: 3,5-Diaminobenzonitrile

To 3,5-dinitrobenzonitrile (5.0 g, 25.89 mmol) in 20 mL of HCl 1M, was added SnCl$_2$ (34.4 g, 7 eq). The reaction mixture was stirred at room temperature for 2 h and then cooled to 0° C. The mixture was made alkaline with a 50% aqueous solution of NaOH and the precipitate was removed by filtration. The filtrate was extracted with ethyl acetate and the combined organic layers were evaporated. The residue and the precipitate were purified by flash chromatography on silica gel (DCM/MeOH//95/5) to yield expected compound as an orange solid (1.95 g, 57% yield). m/z (ESI) 134.0 [M+H]$^+$.

Step B: 3-Amino-5-[(7-chloroquinolin-4-yl)amino] benzonitrile hydrochloride 3,5-Diaminobenzonitrile (500 mg, 3.76 mmol) and 4,7-dichloroquinoline (744 mg, 1 eq) were stirred at room temperature in 50 mL of ethanol for 18 h. The precipitate was removed by filtration to yield expected compound as a yellow powder (925 mg, 74% yield).

$^1$H NMR (300 MHz, DMSO-d$_6$) δ11.08; (br, 1H), 8.83; (d, J=9.2 Hz, 1H), 8.56; (d, J=7.0 Hz, 1H), 8.17; (d, J=2.0 Hz, 1H), 7.87; (dd, J=9.2 and 2.0 Hz, 1H), 7.02-6.98; (m, 1H), 6.95-6.85; (m, 3H), 6.00; (br, 2H); $^{13}$C NMR (75 MHz, DMSO-d$_6$) δ158.2; (C), 154.7; (C), 147.1; (CH), 142.7; (C), 142.3; (C), 142.0; (C), 131.0; (CH), 129.7; (CH), 122.9; (CH), 122.2; (C), 119.6; (C), 118.5; (CH), 118.2; (CH), 117.8; (CH), 116.3; (C), 104.5; (CH).

Example 20

Preparation of 4-[(3-amino-5-cyanophenyl)amino]-7-chloro-1-[2-(piperidin-1-yl)ethyl]quinolin-1-ium chloride (compound 74)

3-Amino-5-[(7-chloroquinolin-4-yl)amino]benzonitrile hydrochloride prepared from step B of example 19 (0.88 g, 2.98 mmol), 1-(2-chloroethyl)piperidine hydrochloride (0.55 g, 1 eq) and K$_2$CO$_3$ (0.83 g, 2 eq) were refluxed in 50 mL of acetonitrile for 48 h. The reaction mixture was then filtered. The filtrate was evaporated to yield expected compound as a yellow powder (0.58 g, 44% yield). m/z (ESI) 406.2 [M]$^+$.

$^1$H NMR (300 MHz, MeOH-d$_4$) δ8.62; (d, J=9.1 Hz, 1H), 8.46; (d, J=7.4 Hz, 1H), 8.39; (d, J=1.9 Hz, 1H), 7.88; (dd, J=9.1 and 1.9 Hz, 1H), 7.10-6.90; (m, 3H), 6.94; (d, J=7.4 Hz, 1H), 4.72; (t, J=6.0 Hz, 2H), 2.83; (t, J=6.0 Hz, 2H), 2.55-2.40; (m, 4H), 1.62-1.40; (m, 6H).

Example 21

Preparation of 3-amino-5-({7-chloro-1-[2-(piperidin-1-yl) ethyl]-1,4-dihydroquinolin-4 ylidene}amino) benzonitrile (compound 75)

3-Amino-5-[(7-chloroquinolin-4-yl)amino]benzonitrile hydrochloride prepared from step B of example 19 (200 mg, 0.68 mmol), 1-(2-chloroethyl)piperidine hydrochloride (125 mg, 1 eq), K$_2$CO$_3$ (468 mg, 5 eq) and DIEA (0.11 mL, 1 eq) were refluxed in 30 mL of acetonitrile for 72 h. The reaction mixture was then filtered. The filtrate was evaporated and the residue was purified by flash chromatography on silica gel (AcOEt/MeOH//100/0 to 95/5) to yield expected compound as a yellow powder (8 mg, 3% yield). m/z (ESI) 406.2 [M+H]$^+$.

$^1$H NMR (300 MHz, MeOH-d$_4$) δ8.37; (d, J=8.8 Hz, 1H), 7.63; (d, J=1.9 Hz, 1H), 7.40-7.28; (m, 2H), 6.70-6.66; (m, 1H), 6.53-6.50; (m, 1H), 6.49-6.46; (m, 1H), 5.88; (d, J=7.9 Hz, 1H), 4.16; (t, J=6.9 Hz, 2H), 2.64; (t, J=6.9 Hz, 2H), 2.52-2.40; (m, 4H), 1.64-1.40; (m, 6H).

Example 22

Preparation of 3-({7-Chloro-1-[2-(piperidin-1-yl) ethyl]-1,4-dihydroquinolin-4-ylidene}amino)-5-{[2-(piperidin-1-yl)ethyl]amino}benzonitrile (compound 76)

3-amino-5-({7-chloro-1-[2-(piperidin-1-yl)ethyl]-1,4-dihydroquinolin-4-ylidene}amino)benzonitrile prepared from example 21 (132 mg, 0.32 mmol), 1-(2-chloroethyl)piperidine hydrochloride (182 mg, 3 eq) and DIEA (0.51 mL, 9.3 eq) were refluxed in 15 mL of 2-methylbutan-1-ol for 10 h. The reaction mixture was then evaporated and the residue and was purified by preparative thin-layer chromatography (DCM/MeOH/NH$_4$OH//95/5/1) to yield expected compound as a yellow oil (28 mg, 17% yield). m/z (ESI) 517.5 [M+H]$^+$.

$^1$H NMR (300 MHz, MeOH-d$_4$) δ 8.37; (d, J=8.8 Hz, 1H), 7.64; (d, J=1.7 Hz, 1H), 7.36; (d, J=8.0 Hz, 1H), 7.32; (dd, J=8.2 and 1.8 Hz, 1H), 6.68-6.59; (m, 1H), 6.50-6.40; (m, 2H), 5.91; (d, J=7.9 Hz, 1H), 4.17; (t, J=6.8 Hz, 2H), 3.25; (t, J=6.8 Hz, 2H), 2.73-2.35; (m, 12H), 1.70-1.40; (m, 12H); $^{13}$C NMR (75 MHz, MeOH-d$_4$) δ 156.6; (C), 153.9; (C), 151.0; (C), 142.1; (CH), 140.3; (C), 137.8; (C), 127.5; (CH), 124.1; (CH), 123.0; (C), 120.0; (C), 115.5; (CH), 113.5; (CH), 113.4; (C), 110.4; (CH), 110.0; (CH), 100.8; (CH), 57.7; (CH$_2$), 56.7; (CH$_2$), 54.8; (CH$_2$), 54.6; (CH$_2$), 49.8; (CH$_2$), 40.2; (CH$_2$), 25.9; (CH$_2$), 25.6; (CH$_2$), 24.2; (CH$_2$), 24.1; (CH$_2$).

Example 23

Preparation of 3-[(7-chloroquinolin-4-yl)amino]-5-{[2-(piperidin-1-yl)ethyl]amino}benzonitrile (compound 77)

Step A: 3-amino-5-{[2-(piperidin-1-yl)ethyl]amino}benzonitrile 3,5-Diaminobenzonitrile prepared from step A of example 19 (511 mg, 3.84 mmol), 1-(2-chloroethyl)piperidine hydrochloride (707 mg, 1 eq) and DIEA (1.97 mL, 3 eq) were refluxed in 50 mL of 2-methylbutan-1-ol for 24 h. The reaction mixture was then evaporated to give 751 mg of expected compound which was used in the next step without further purification. m/z (ESI) 245.3 [M+H]$^+$.

Step B: 3-[(7-chloroquinolin-4-yl)amino]-5-{[2-(piperidin-1-yl)ethyl]amino}benzonitrile 3-amino-5-{[2-(piperidin-1-yl)ethyl]amino}benzonitrile (200 mg, 0.82 mmol) and 4,7-dichloroquinoline (162 mg, 1 eq) were refluxed in 15 mL of ethanol and 0.82 mL of HCl 1M for 24 h. The reaction mixture was then evaporated and the residue and was purified by preparative thin-layer chromatography (DCM/MeOH/NH$_4$OH//95/5/1) to yield expected compound as a yellow powder (51 mg, 15% yield). m/z (ESI) 406.3 [M+H]$^+$.

$^1$H NMR (300 MHz, CDCl$_3$) δ 8.40; (d, J=5.4 Hz, 1H), 7.92; (d, J=9.1 Hz, 1H), 7.83; (d, J=2.1 Hz, 1H), 7.24; (dd, J=9.0 and 2.1 Hz, 1H), 6.89; (d, J=5.4 Hz, 1H), 6.72-6.69; (m, 1H), 6.68-6.63; (m, 1H), 6.50-6.43; (m, 1H), 4.97; (br, 1H), 4.60; (br, 1H), 3.10-2.97; (m, 2H), 2.57-2.47; (m, 2H), 2.43-2.22; (m, 4H), 1.57-1.43; (m, 4H), 1.41-1.30; (m, 2H); $^{13}$C NMR (75 MHz, CDCl$_3$) δ 151.3; (CH), 149.7; (C), 149.1; (C), 147.3; (C), 141.7; (C), 135.5; (C), 128.1; (CH), 126.2; (CH), 122.1; (CH), 119.0; (C), 118.4; (C), 113.5; (C), 113.2; (CH), 111.1; (CH), 109.8; (CH), 103.4; (CH), 56.2; (CH$_2$), 53.9; (CH$_2$), 39.2; (CH$_2$), 24.9; (CH$_2$), 23.6; (CH$_2$).

Example 24

Preparation of 4-[(7-chloroquinolin-4-yl)amino]-2,6-bis(pyrrolidin-1-ylmethyl)phenol (compound 78)

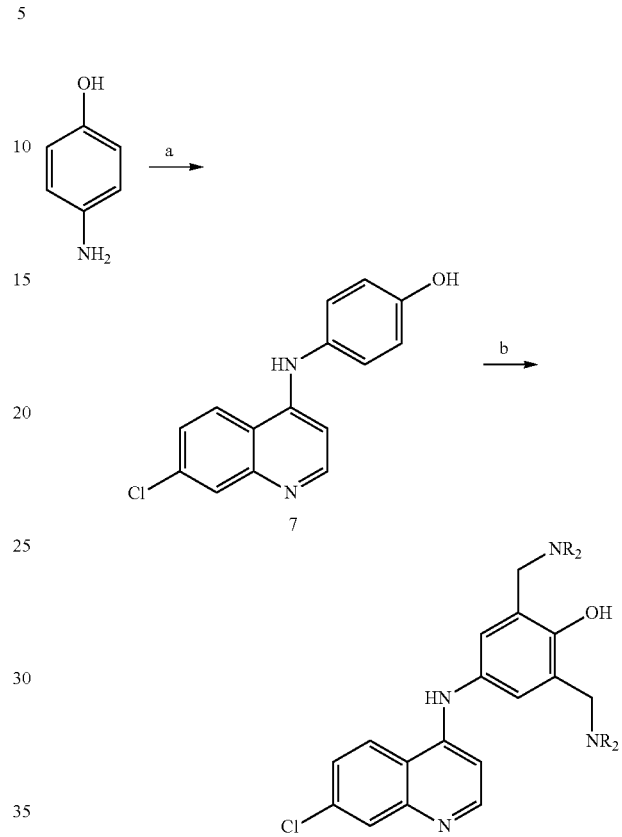

$^c$Reagents:
a 4,7-dichloroquinoline, EtOH, reflux;
b HCHO, amine, EtOH, r.t.

Step A: 4-[(7-Chloroquinolin-4-yl)amino]phenol 4-aminophenol (1.09 g, 10 mmol) and 4,7-dichloroquinoline (1.98 g, 1 eq) were refluxed in 50 mL of ethanol for 2 h. The reaction mixture was then cooled to room temperature and the precipitate was removed by filtration and washed successively with a saturated aqueous solution of NaHCO$_3$, water, methanol and then petroleum ether to yield expected compound as a yellow powder (2.57 g, 95% yield). LC-MS: m/z (ESI) 271.1 [M+H]$^+$.

$^1$H NMR (300 MHz, DMSO-d$_6$) δ 10.7; (br, 1H), 9.88; (br, 1H), 8.77; (d, J=9.1 Hz, 1H), 8.43; (d, J=6.8 Hz, 1H), 8.09; (d, J=2.1 Hz, 1H), 7.77; (dd, J=9.1 and 2.1 Hz, 1H), 7.23; (d, J=8.8 Hz, 1H), 6.94; (d, J=8.8 Hz, 1H), 6.60; (d, J=6.8 Hz, 1H).

Step B: 4-[(7-Chloroquinolin-4-yl)amino]-2,6-bis(pyrrolidin-1-ylmethyl)phenol 4-[(7-chloroquinolin-4-yl)amino]phenol (2.45 g, 9 mmol), pyrrolidine (3.25 mL, 4.4 eq) and a 37% aqueous solution of formaldehyde (3 mL, 4.4 eq) were stirred at room temperature for 18 h in 5 mL of ethanol. The reaction mixture was then evaporated and the residue was purified by flash chromatography (DCM/MeOH/NH$_4$OH 8:2:0.1) to yield expected compound as a brown solid (2.90 g, 74% yield). LC-MS: m/z (ESI) 437.1 [M+H]$^+$.

$^1$H NMR (300 MHz, DMSO-d$_6$) δ8.91; (br, 1H), 8.41; (d, J=9.0 Hz, 1H), 8.36; (d, J=5.4 Hz, 1H), 7.84; (d, J=2.1 Hz, 1H), 7.51; (dd, J=9.0 and 2.1 Hz, 1H), 7.06; (s, 2H), 6.60; (d, J=5.4 Hz, 1H), 2.68-2.52; (m, 8H), 1.83-1.60; (m, 8H).

Example 25

Preparation of 4-[(7-chloroquinolin-4-yl)amino]-2,6-bis(morpholin-1-ylmethyl)phenol (compound 79)

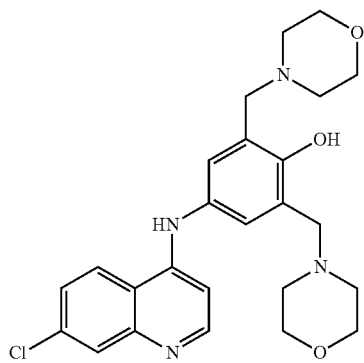 [SMILES: Oc1c(CN2CCOCC2)cc(Nc2ccnc3cc(Cl)ccc23)cc1CN1CCOCC1]

4-[(7-Chloroquinolin-4-yl)amino]phenol (of example 24—step A) (0.292 g, 1.08 mmol), morpholine (0.89 mL, 8.8 eq) and a 37% aqueous solution of formaldehyde (0.715 mL, 8.8 eq) were refluxed for 24 h in 5 mL of ethanol. The reaction mixture was then evaporated and the residue was washed with pentane to yield expected compound as a pale yellow solid (0.506 g, 40% yield). LC-MS: m/z (ESI) 469.2-471.2 [M+H]$^+$.

$^1$H NMR (300 MHz, DMSO-d$_6$) δ8.95; (s, 1H), 8.41; (d, J=9.0 Hz, 1H), 8.37; (d, J=5.4 Hz, 1H), 7.84; (d, J=2.2 Hz, 1H), 7.53; (dd, J=9.0 Hz and 2.0 Hz, 1H), 7.08; (s, 2H), 6.59; (d, J=5.4 Hz, 1H), 3.5-3.7; (m, 12H), 2.4-2.6; (m, 8H); $^{13}$C NMR (300 MHz, CDCl$_3$) δ154.3; (C), 151.3; (CH), 149.7; (C), 149.0; (C), 135.5; (C), 130.0; (C), 128.3; (CH), 126.2; (CH), 125.5; (2CH), 123.7; (2C), 121.6; (CH), 117.5; (C), 101.3; (CH), 66.9; (4CH$_2$), 59.1; (2CH$_2$), 53.3; (4CH$_2$).

Example 26

Preparation of 4-[(7-chloroquinolin-4-yl)amino]-2,6-bis(4-methylpiperazin-1-ylmethyl)phenol (compound 80)

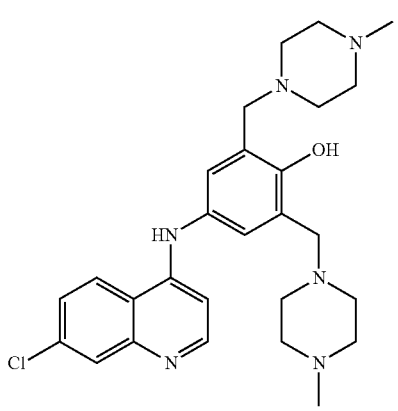 [SMILES: CN1CCN(Cc2cc(Nc3ccnc4cc(Cl)ccc34)cc(CN3CCN(C)CC3)c2O)CC1]

4-[(7-Chloroquinolin-4-yl)amino]phenol (of example 24—step A) (0.20 g, 0.74 mmol), N-methylpiperazine (0.725 mL, 8.8 eq) and a 37% aqueous solution of formaldehyde (0.49 mL, 8.8 eq) were refluxed for 24 h in 5 mL of ethanol. The reaction mixture was then evaporated and the residue was washed with pentane to yield expected compound as a pale yellow solid (0.392 g, 97% yield). LC-MS: m/z (ESI) 495.3-497.3 [M+H]$^+$.

$^1$H NMR (300 MHz, MeOH-d$_4$) δ8.39; (d, J=5.7 Hz, 1H), 8.37; (d, J=5.7 Hz, 1H), 7.93; (d, J=2.1 Hz, 1H), 7.60; (dd, J=9.0 Hz and 2.1 Hz, 1H), 7.22; (s, 2H), 6.76; (d, J=5.7 Hz, 1H), 3.84; (s, 4H), 3.4-3.5; (m, 16H), 2.6-2.8; (m, 16H), 2.44; (s, 6H); $^{13}$C NMR (300 MHz, DMSO-d$_6$) δ153.8; (C), 152.4; (CH), 150.0; (C), 134.3; (C), 130.7; (C), 128.0; (CH), 125.1; (CH), 124.8; (CH), 123.8; (C), 118.2; (C), 100.9; (CH), 57.5; (CH$_2$), 54.4; (CH$_2$), 51.8; (CH$_2$), 45.2; (CH$_3$).

Example 27

Preparation of 5-[(7-chloroquinolin-4-yl)amino]-2-(pyrrolidin-1-ylmethyl)phenol (compound 81) and 5-[(7-chloroquinolin-4-yl)amino]-2-(morpholin-4-ylmethyl)phenol (compound 82)

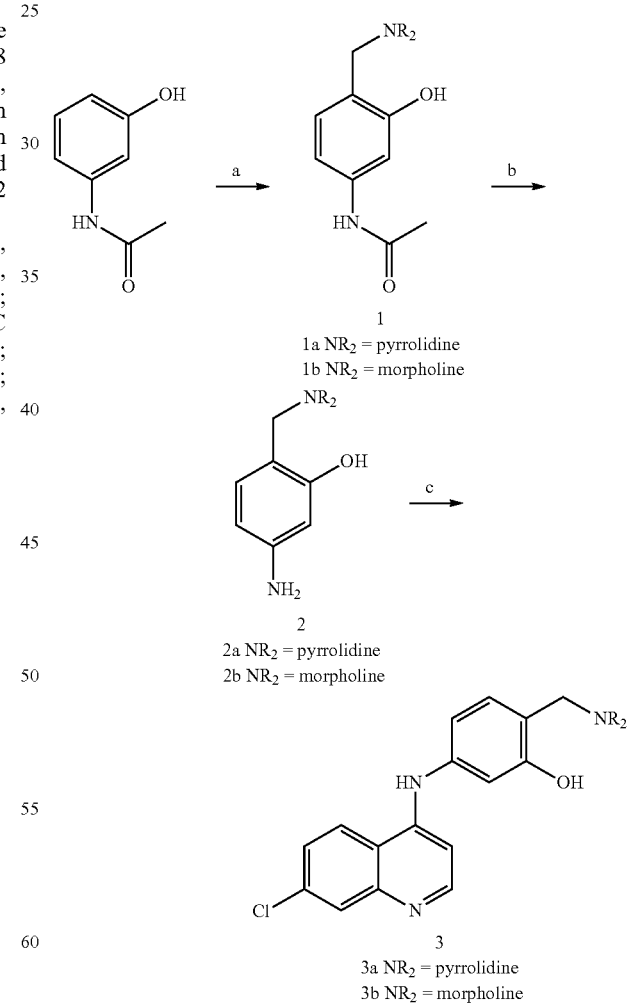

$^c$Reagents:
a HCHO, NHR$_2$, EtOH; reflux;
b HCl 20%, reflux;
c 4,7-dichloroquinoline, EtOH, reflux.

Example 27.1

Preparation of 5-[(7-chloroquinolin-4-yl)amino]-2-(pyrrolidin-1-ylmethyl)phenol (compound 81)

Step A: N-[3-hydroxy-4-(pyrrolidin-1-ylmethyl)phenyl]acetamide

N-(3-hydroxyphenyl)acetamide (0.50 g, 3.31 mmol), formaldehyde 37% in water (678 µL, 2.7 eq), and pyrrolidine (276 µL, 1 eq) were dissolved in 10 mL of EtOH. The reaction mixture was refluxed overnight, evaporated and purified by flash chromatography (DCM/MeOH/NH$_4$OH 9.6:0.4:0.1) to yield expected compound as a pale yellow oil (224 mg, 29% yield). LC-MS: m/z (ESI) 235.13 [M+H]$^+$

Step B: 5-amino-2-(pyrrolidin-1-ylmethyl)phenol

N-[3-hydroxy-4-(pyrrolidin-1-ylmethyl)phenyl]acetamide (0.14 g, 0.61 mmol), hydrochloric acid 20% (1 mL). The mixture was refluxed 6 h, evaporated and used for the next step.

Step C: 5-[(7-chloroquinolin-4-yl)amino]-2-(pyrrolidin-1-ylmethyl)phenol 5-amino-2-(pyrrolidin-1-ylmethyl)phenol (117 mg, 0.61 mmol) and 4,7-dichloroquinoline (143 mg, 1 eq) were refluxed overnight in 1 mL of EtOH. The reaction mixture was then evaporated and purified by flash chromatography (DCM/MeOH/NH$_4$OH 9:1:0.1) to yield expected compound as a yellow solid (92 mg, 29% yield). LC-MS: m/z (ESI) 354.1-356.1 [M+H]$^+$ $^1$H NMR (300 MHz, MeOH-d$_4$) δ8.38; (d, J=5.6 Hz, 1H), 8.26; (d, J=9 Hz, 1H), 7.85; (d, J=2 Hz, 1H), 7.49; (dd, J=9.1 and 2.1 Hz, 1H), 7.19; (d, J=8.0 Hz, 1H), 7.01; (d, J=5.7 Hz, 1H), 6.75-6.85; (m, 2H), 4.01; (s, 2H), 2.85-2.95; (m, 4H), 1.9-2.0; (m, 4H)

Example 27.2

Preparation of 5-[(7-chloroquinolin-4-yl)amino]-2-(morpholin-4-ylmethyl)phenol (compound 82)

Step A: N-[3-hydroxy-4-(morpholin-4-yl)phenyl]acetamide

N-(3-hydroxyphenyl)acetamide (0.50 g, 3.31 mmol), formaldehyde 37% (678 µL, 2.7 eq), and morpholine (290 µL, 1 eq) were dissolved in 10 mL of EtOH. The reaction mixture was refluxed overnight, evaporated and purified by flash chromatography (DCM/MeOH/NH$_4$OH 9.6:0.4:0.1) to yield expected compound as a pale yellow oil (107 mg, 13% yield). LC-MS: m/z (ESI) 251.3 [M+H]$^+$; $^1$H NMR (300 MHz, MeOH-d$_4$) δ7.09; (d, J=1.3 Hz, 1H), 6.8-6.9; (m, 2H), 3.6-3.7; (m, 4H), 3.58; (s, 2H), 2.4-2.5; (m, 4H), 2.0; (s, 3H)

Step B: 5-amino-2-(morpholin-4-ylmethyl)phenol

N-[3-hydroxy-4-(morpholin-4-yl)phenyl]acetamide (0.073 g, 0.292 mmol), hydrochloric acid 20% (1 mL). The mixture was refluxed 6 h. The reaction mixture was then evaporated and purified by flash chromatography (DCM/MeOH/9.6:0.4) to yield expected compound as a pale yellow oil (0.073 mg, 22% yield) which was used directly for the next step.

Step C: 5-[(7-chloroquinolin-4-yl)amino]-2-(morpholin-4-ylmethyl)phenol 5-amino-2-(morpholin-4-ylmethyl)phenol (58 mg, 0.28 mmol) and 4,7-dichloroquinoline (61 mg, 1.1 eq) were refluxed overnight in 1 mL of EtOH. The reaction mixture was then evaporated and purified by flash chromatography (DCM/MeOH/NH$_4$OH 9:1:0.1) to yield expected compound as a brown solid (41 mg, 40% yield). LC-MS: m/z (ESI) 470.1-472.1 [M+H]$^+$ $^1$H NMR (300 MHz, CDCl$_3$) δ8.56; (d, J=5.1 Hz, 1H), 8.02; (d, J=2.1 Hz, 1H), 7.84; (d, J=9.0 Hz, 1H), 7.45; (dd, J=9.0 and 2.1 Hz, 1H), 7.05; (d, J=5.1 Hz, 1H), 7.01; (d, J=8.1 Hz, 1H), 6.76; (d, J=2.1 Hz, 1H), 6.71; (dd, J=8.1 and 2.1 Hz, 1H), 6.56; (sl, 1H), 3.5-3.7; (m, 6H), 2.5-2.6; (m, 4H).

Example 28

Preparation of 3-[(7-chloroquinolin-4-yl)amino]-2-(4-methylpiperazin-1-ylmethyl)phenol (compound 83)

Step A: 3-[(7-chloroquinolin-4-yl)amino]phenol 3-aminophenol (5.00 g, 25.25 mmol) and 4,7-dichloroquinoline (2.76 g, 1 eq) were refluxed overnight in 5 mL of EtOH. The reaction mixture was then evaporated and purified by flash chromatography (DCM/MeOH/NH$_4$OH 9:1:0.1) to yield expected compound as a pale yellow solid (6.8 g, 99% yield). LC-MS: m/z (ESI) 271.2 [M+H]$^+$;

Step B: 3-[(7-chloroquinolin-4-yl)amino]-2-(4-methylpiperazin-1-ylmethyl) phenol 3-[(7-chloroquinolin-4-yl)amino]phenol (0.20 g, 0.74 mmol), formaldehyde 37% (62 µL, 1.1 eq), and N-methylpiperazine (90 µL, 1.1 eq) was dissolved in 1 mL of EtOH. The mixture was refluxed overnight, evaporated and purified by flash chromatography (DCM/MeOH/NH$_4$OH 7.5:2.5:0.2) to yield expected compound as a pale yellow oil (42 mg, 15% yield). LC-MS: m/z (ESI) 383.3-385.3 [M+H]$^+$ $^1$H NMR (300 MHz, MeOH-d$_4$) δ8.36; (d, J=5.6 Hz, 1H), 8.26; (d, J=9 Hz, 1H), 7.84; (d, J=2 Hz, 1H), 7.48; (dd, J=9 and 2.2 Hz, 1H), 7.11; (d, J=8.0 Hz, 1H), 6.96; (d, J=5.6 Hz, 1H), 6.7-6.8; (m, 2H), 3.75; (s, 2H), 2.4-2.8; (m, 8H), 2.32; (s, 3H)

Example 29

Preparation of 7-chloro-N-(3-((diethylamino)methyl)-4-fluorophenyl)quinolin-4-amine (compound 84)

Step A: (2-Fluoro-5-nitro-phenyl)-methanol

To a solution of 2-fluoro-5-nitro-benzaldehyde (1000 mg, 5.91 mmoles) in MeOH (10 mL) was added NaBH$_4$ (182 mg, 4.82 mmoles). The reaction mixture was stirred for 3 h at 0° C. The reaction mixture was acidified with HCl 1M until pH4, concentrated. 50 mL of water was added and the compound was extracted with Et$_2$O. The organic layer was dried over MgSO$_4$, filtered, evaporated. Expected compound was obtained as a pale yellow solid (1007 mg, 99% yield). mp=62-64° C. $^1$H NMR (300 MHz, CDCl$_3$) δ8.43; (dd, 6-CH, J=6.2 Hz and 2.9 Hz, 1H), 8.19; (ddd, J=9 Hz, 4.5 Hz and 2.9 Hz, 1H), 7.20; (dd, J=9.0 Hz and 9.0 Hz, 1H), 4.85; (d, J=3.6 Hz, 2H), 2.12; (s large, 1H). $^{13}$C NMR (75 MHz, CDCl$_3$) δ125.0; (CH, d, J=10.0 Hz), 124.7; (CH, d, J=6.9 Hz), 116.2; (CH, d, J=23.6 Hz), 58.2; (CH$_2$).

Step B: Toluene-4-sulfonic acid 2-fluoro-5-nitro-benzyl ester

To a solution of NaOH (0.537 g, 13.42 mmoles) in H$_2$O (4 mL) was added a solution of 2-fluoro-5-nitro-phenyl)-methanol (0.999 g, 5.84 mmoles) in THF (20 mL) at 0° C. A solution of TsCl (1.892 g, 9.92 mmoles) in THF (10 mL) is then added dropwise. The reaction mixture was stirred for 2 h at 5-10° C. 50 mL of water was added and the compound was extracted with CH$_2$Cl$_2$ (3×100 mL). The organic layer was dried over MgSO$_4$, filtered, evaporated. Expected compound was precipited with MeOH and purified by TLC (Hex/AcOEt//7/3) and obtained as a white solid (1.700 g, 90% yield). mp=89-91° C. $^1$H NMR (300 MHz, CDCl$_3$) δ8.18-8.26; (m, 2H), 7.82; (m, 2H), 7.35; (m, 2H), 7.20; (dd, J=8.7 Hz et 8.7 Hz, 1H), 5.17; (s, 2H), 2.46; (s, 3H). $^{13}$C NMR (75 MHz, CDCl$_3$) δ130.1; (CH), 128.1; (CH), 126.7; (CH, d, J=10.0 Hz), 126.3; (CH, d, J=5.0 Hz), 116.7; (CH, d, J=23.6 Hz), 64.1; (CH$_2$), 22.2; (CH$_3$).

Step C: Diethyl-(2-fluoro-5-nitro-benzyl)-amine

To a solution of toluene-4-sulfonic acid 2-fluoro-5-nitro-benzyl ester (0.696 g, 2.13 mmoles) in 1,4-dioxane (4 mL) was added TEA (0.45 mL, 3.20 mmoles) and diethylamine (0.33 mL, 3.21 mmoles). The reaction mixture was stirred for 8 h at 55° C., concentrated and purified by TLC (petroleum ether/AcOEt/NH$_4$OH//8/2/0.2). The expected compound was obtained as a yellow oil (0.365 g, 76% yield). MALDI-TOF: m/z 227.1 [M+H]$^+$. $^1$H NMR (300 MHz, CDCl$_3$) δ8.44; (dd, J=6.3 Hz and 2.9 Hz, 1H), 8.12; (ddd, 4-CH, J=8.9 Hz, 2.9 Hz and 4.4 Hz, 1H), 7.15; (dd, J=8.9 Hz and 8.9 Hz, 1H), 3.67; (s, 2H), 2.58; (q, J=7.1 Hz, 4H), 1.08; (t, J=7.1 Hz, 6H). $^{13}$C NMR (75 MHz, CDCl$_3$) δ126.7; (CH, d, J=6.9 Hz), 124.1; (CH, d, J=10.2 Hz), 115.9; (CH, d, J=24.6 Hz), 49.6; (CH$_2$), 47.1; (CH$_2$), 11.8; (CH$_3$).

Step D: 3-((diethylamino)methyl)-4-fluorobenzenamine

To a solution of diethyl-(2-fluoro-5-nitro-benzyl)-amine (0.155 mg, 0.69 mmoles) in THF (20 mL) was added a solution of SnCl$_2$ (520 mg, 2.74 mmoles) in THF (5 mL) and HCl 1M (2.1 mL). The reaction mixture was refluxed for 8 h and concentrated. Saturated solution of NaHCO$_3$ was added until pH8. Aqueous layer was extracted with CH$_2$Cl$_2$ (5×50 mL). The organic layer was dried over MgSO$_4$, filtered, evaporated. Expected compound was precipited with MeOH and purified by TLC DCM/MeOH/NH$_4$OH//9/1/0.2) and obtained as a yellow oil (98 mg, 73% yield). MALDI-TOF: m/z 197.2 [M+H]$^+$. $^1$H NMR (300 MHz, CDCl$_3$) δ6.80; (dd, J=8.7 Hz and 8.7 Hz, 1H), 6.75; (dd, J=5.7 Hz and 3.0, 1H), 6.49; (ddd, J=8.7 Hz, 3.9 Hz and 3.0 Hz, 1H), 3.65-3.75; (s large, 2H), 3.57; (s, 2H), 2.57; (q, J=7.2 Hz, 4H), 1.07; (t, J=7.2 Hz, 6H). $^{13}$C NMR (75 MHz, CDCl$_3$) δ118.2; (CH, d, J=3.8 Hz), 116.4; (CH, d, J=23.3 Hz), 115.7; (CH, d, J=7.9 Hz), 49.8; (CH$_2$), 47.3; (CH$_2$), 12.4; (CH$_3$).

Step E: 7-chloro-N-(3-((diethylamino)methyl)-4-fluorophenyl)quinolin-4-amine To a solution of 3-((diethylamino)methyl)-4-fluorobenzenamine (98.3 mg, 0.50 mmoles) in acetonitrile (10 mL) was added a solution of 4,7-dichloroquinoleine (99.2 mg, 0.50 mmoles) in acetonitrile (5 mL) and HCl 1M (0.5 mL). The reaction mixture was refluxed overnight, concentrated and purified by TLC (DCM/MeOH/NH$_4$OH//9.5/0.5/0.2). Expected compound was obtained as a white solid (163 mg, 91% yield). MALDI-TOF: m/z 358.3-360.2 [M+H]$^+$. $^1$H NMR (300 MHz, CDCl$_3$) δ8.50; (d, J=5.4 Hz, 1H), 8.00; (d, J=2.1 Hz, 1H), 7.93; (d, J=9.0 Hz, 1H), 7.47; (dd, J=6.3 Hz and 2.8 Hz, 1H), 7.42; (dd, J=9.0 Hz and 2.2 Hz, 1H), 7.21; (ddd, J=8.8 Hz, 4.5 Hz and 2.8 Hz, 1H), 7.08; (dd, J=8.8 Hz and 8.8 Hz, 1H), 6.79; (d, J=5.4 Hz, 1H), 3.71; (s, 2H), 2.65; (q, J=7.2 Hz, 4H), 1.10; (t, J=7.2 Hz, 6H). $^{13}$C NMR (75 MHz, CDCl$_3$) δ151.6; (CH), 128.6; (CH), 126.4; (CH, d, J=3.9 Hz), 126.1; (CH), 123.9; (CH, d, J=8.5 Hz), 121.5; (CH), 116.3; (CH, d, J=23.7 Hz), 101.9; (CH), 49.6; (CH$_2$), 47.0; (CH$_2$), 11.4; (CH$_3$).

Example 30

Preparation of 7-chloro-N-(4-fluoro-3-(pyrrolidin-1-ylmethyl)phenyl)quinolin-4-amine (compound 85)

Step A: 1-(2-Fluoro-5-nitro-benzyl)-pyrrolidine

To a solution of toluene-4-sulfonic acid 2-fluoro-5-nitro-benzyl ester (compound of step B of example 29) (0.696 g, 2.31 mmoles) in 1,4-dioxane (20 mL) was added TEA (0.32 mL, 2.31 mmoles) and pyrrolidine (0.19 mL, 2.31 mmoles). The reaction mixture was stirred for 24 h at room temperature, concentrated and purified by TLC (petroleum ether/AcOEt/NH$_4$OH//8/2/0.2). The expected compound was obtained as a yellow oil (0.399 g, 77% yield). MALDI-TOF: m/z 225.1 [M+H]$^+$. $^1$H NMR (300 MHz, CDCl$_3$) δ8.38; (dd, J=6.2 Hz and 2.9 Hz, 1H), 8.15; (ddd, 4-CH, J=8.9 Hz, 2.9 Hz and 4.4 Hz, 1H), 7.17; (dd, J=8.9 Hz and 8.9 Hz, 1H), 3.76; (s, 2H), 2.5-2.6; (m, 4H), 1.8-1.9; (m, 4H). $^{13}$C NMR (75 MHz, CDCl$_3$) δ127.0; (CH, d, J=6.4 Hz), 124.5; (CH, d, J=10.1 Hz), 116.2; (CH, d, J=24.9 Hz), 54.1; (CH$_2$), 52.2; (CH$_2$), 23.5; (CH$_2$).

Step B: 4-Fluoro-3-(pyrrolidin-1-ylmethyl)benzenamine

To a solution of 1-(2-fluoro-5-nitro-benzyl)-pyrrolidine (420 mg, 1.87 mmol) in THF (20 mL) was added a solution of SnCl$_2$ (1421 mg, 7.49 mmol) in THF (5 mL) and HCl 1M (2.1 mL). The reaction mixture was refluxed for 4 h and concentrated. Saturated solution of NaHCO$_3$ was added until pH8. Aqueous layer was extracted with CH$_2$Cl$_2$ (5×50 mL). The organic layer was dried over MgSO$_4$, filtered, evaporated. Expected compound was precipitated with MeOH and purified by TLC (DCM/MeOH/NH$_4$OH//9.5/0.5/0.35) and obtained as a yellow oil (229.5 mg, 63% yield). MALDI-TOF: m/z 195.2 [M+H]$^+$. $^1$H NMR (300 MHz, CDCl$_3$) δ6.76; (dd, J=9.5 Hz and 8.7 Hz, 1H), 6.69; (dd, J=6.1 Hz and 2.9 Hz, 1H), 6.46; (ddd, J=8.7 Hz, 4.1 Hz and 2.9 Hz, 1H), 3.57; (d, J=1.6 Hz, 2H), 3.3-3.5; (s large, 2H), 2.5-2.6; (m, 2H), 1.7-1.8; (m, 4H). $^{13}$C NMR (75 MHz, CDCl$_3$) δ117.5; (CH, d, J=3.5 Hz), 115.7; (CH, d, J=23.6 Hz), 115.0; (CH, d, J=7.7 Hz), 54.1; (CH$_2$), 52.8; (CH$_2$), 23.6; (CH$_2$).

Step C: 7-Chloro-N-(4-fluoro-3-(pyrrolidin-1-ylmethyl)phenyl)quinolin-4-amine To a solution of 4-fluoro-3-(pyrrolidin-1-ylmethyl)benzenamine (199.4 mg, 1.03 mmoles) in acetonitrile (40 mL) was added a solution of 4,7-dichloroquinoleine (203.3 mg, 1.03 mmoles) in acetonitrile (5 mL) and HCl 1M (1.12 mL). The reaction mixture was refluxed for 2 h, concentrated and purified by TLC (DCM/MeOH/NH₄OH//9/1/0.2). Expected compound was obtained as a white solid (330.4 mg, 90% yield). MALDI-TOF: m/z 356.2-358.1 [M+H]⁺. ¹H NMR (300 MHz, CDCl₃) δ8.36; (d, J=5.6 Hz, 1H), 8.26; (d, J=9.1 Hz, 1H), 7.85; (d, J=2.1 Hz, 1H), 7.48; (dd, J=9.1 Hz and 2.1 Hz, 1H), 7.40; (dd, J=6.4 Hz and 2.8 Hz, 1H), 7.31; (ddd, J=8.7 Hz, 4.5 Hz and 2.8 Hz, 1H), 7.18; (dd, J=8.8 Hz and 8.8 Hz, 1H), 6.82; (d, J=5.6 Hz, 1H), 3.74; (s, 2H), 2.6-2.7; (m, 4H), 1.8-1.9; (m, 4H). ¹³C NMR (75 MHz, CDCl₃) δ149.7; (CH), 125.8; (CH), 125.1; (CH), 124.0; (CH), 123.5; (CH, d, J=8.8 Hz), 121.8; (CH), 114.6; (CH, d, J=23.9 Hz), 99.6; (CH), 52.1; (CH₂), 50.5; (CH₂), 21.4; (CH₂).

Example 31

Preparation of 7-chloro-N-[4-(morpholin-4-yl)-3-(pyrrolidin-1-ylmethyl)phenyl]quinolin-4-amine (compound 86)

Step A: [2-(Morpholin-4-yl)-5-nitrophenyl]methanol

2-Fluoro-5-nitrobenzyl alcohol (1 g, 5.84 mmol) and morpholine (1.03 mL, 11.68 mmol) were heated at 115° C. for 1 h. The reaction mixture was then diluted with 40 mL of THF and washed with a saturated aqueous solution of Na₂CO₃ and then with brine. The organic layer was dried over MgSO₄, filtered and evaporated to yield expected compound as yellow oil (1.38 g, 99% yield). MALDI-TOF: m/z 239.2 [M+H]⁺.
¹H NMR (300 MHz, MeOH-d₄) δ8.44; (d, J=2.7 Hz, 1H), 8.16; (dd, J=9.0 and 2.8 Hz, 1H), 7.23; (d, J=8.7 Hz, 1H), 4.75; (s, 2H), 3.89; (t, J=4.7 Hz, 4H), 3.09; (t, J=4.7 Hz, 4H); ¹³C NMR (75 MHz, MeOH-d₄) δ156.5; (C), 143.4; (C), 136.6; (C), 124.1; (CH), 123.5; (CH), 118.8; (CH), 67.0; (CH₂), 59.4; (CH₂), 52.6; (CH₂).

Step B: [5-Amino-2-(morpholin-4-yl)phenyl]methanol

[2-(Morpholin-4-yl)-5-nitrophenyl]methanol (1.38 g, 5.80 mmol) was hydrogenated using ammonium formate (3.67 g, 58 mmol) and Pd/C (10% Pd, 0.62 g, 0.58 mmol) in 50 mL of EtOH. The mixture was stirred for 1 h at room temperature and then filtered through a celite pad. The filtrate was evaporated and the residue was dissolved in DCM and washed with a saturated aqueous solution of Na₂CO₃. The aqueous layer was extracted with DCM. The combined organic layers were dried over MgSO₄, filtered and evaporated to yield expected compound as a brown powder (1.21 g, 99% yield). LC-MS: m/z (ESI) 209.2 [M+H]⁺. ¹H NMR (300 MHz, MeOH-d₄) δ7.02; (d, J=15.0 Hz, 1H), 6.83; (d, J=9.0 Hz, 1H), 6.68; (dd, J=6.0 Hz, 1H), 4.71; (s, 2H), 3.82; (t, J=4.5 Hz, 4H), 2.87; (t, J=4.7 Hz, 4H).

Step C: {5-[(7-chloroquinolin-4-yl)amino]-2-(morpholin-4-yl)phenyl}methanol hydrochloride

[5-Amino-2-(morpholin-4-yl)phenyl]methanol (1.21 g, 5.80 mmol) and 4,7-dichloroquinoline (1.38 g, 6.98 mmol) were refluxed in 10 mL of n-pentanol for 3 h. The reaction mixture was then cooled to room temperature and the hydrochloride precipitate was removed by filtration to yield expected compound as a yellow powder (1.90 g, 80% yield). LC-MS: m/z (ESI) 370.3 [M+H]⁺.
¹H NMR (300 MHz, MeOH-d₄) δ8.55; (d, J=9.0 Hz, 1H), 8.33; (d, J=6.9 Hz, 1H), 7.93; (d, J=1.8 Hz, 1H), 7.77; (dd, J=9.0 and 2.1 Hz, 1H), 7.58-7.56; (m, 1H), 7.40-7.28; (m, 2H), 6.86; (d, J=7.2 Hz, 1H), 4.78; (s, 2H), 3.85; (t, J=4.5 Hz, 4H), 2.97; (t, J=4.5 Hz, 4H).

Step D: 7-chloro-N-[4-(morpholin-4-yl)-3-(pyrrolidin-1-ylmethyl)phenyl]quinolin-4-amine To a suspension of {5-[(7-chloroquinolin-4-yl)amino]-2-(morpholin-4-yl)phenyl}methanol hydrochloride (0.105 g, 0.26 mmol) in 4 mL of NMP at 0° C. was added thionyl chloride (90 μL, 1.23 mmol). The reaction mixture was warmed up to room temperature and stirred for 3 h. The reaction mixture was then slowly added to pyrrolidine (0.65 mL, 7.75 mmol) in 1 mL of NMP at 0° C. and then stirred at room temperature for 2 h. This solution was diluted in 100 mL of CH₂Cl₂ and washed with a saturated aqueous solution of NaHCO₃. The organic layer was dried over MgSO₄, filtered, evaporated and purified by flash chromatography (DCM/MeOH/NH₄OH//90/10/1) to yield expected compound as a yellow solid (105 mg, 96% yield). LC-MS: m/z (ESI) 423.3 [M+H]⁺. mp=187-188° C.
¹H NMR (300 MHz, CDCl₃) δ8.47; (d, J=5.4 Hz, 1H), 7.95; (d, J=2.1 Hz, 1H), 7.94; (d, J=8.7 Hz, 1H), 7.40; (d, J=2.4 Hz, 1H), 7.37; (dd, J=8.7 and 2.1 Hz, 1H), 7.18; (dd, J=8.4 and 2.4 Hz, 1H), 7.08; (d, J=8.4 Hz, 1H), 6.83; (d, J=5.4 Hz, 1H), 3.88-3.84; (m, 4H), 3.70; (s, 2H), 2.99-2.96; (m, 4H), 2.54-2.52; (m, 4H), 1.76-1.73; (m, 4H); ¹³C NMR (75 MHz, CDCl₃) δ152.0; (CH), 128.8; (CH), 125.9; (2×CH), 122.9; (CH), 121.9; (CH), 120.7; (CH), 102.0; (CH), 67.6; (CH₂), 55.0; (CH₂), 54.4; (CH₂), 53.4; (CH₂), 23.7; (CH₂).

Example 32

Preparation of 7-chloro-N-{3-[(4-methylpiperazin-1-yl)methyl]-4-(morpholin-4-yl)phenyl}quinolin-4-amine (compound 87)

To a suspension of {5-[(7-chloroquinolin-4-yl)amino]-2-(morpholin-4-yl)phenyl}methanol hydrochloride (compound of step C of example 31) (0.105 g, 0.26 mmol) in 4 mL of NMP at 0° C. was added thionyl chloride (90 μL, 1.23 mmol). The reaction mixture was warmed up to room temperature and stirred for 3 h. The reaction mixture was then slowly added to 4-methylpiperazine (0.86 mL, 7.75 mmol) in 1 mL of NMP at 0° C. and then stirred at room temperature for 2 h. This solution was diluted in 100 mL of CH₂Cl₂ and washed with a saturated aqueous solution of NaHCO₃. The organic layer was dried over MgSO₄, filtered, evaporated and purified by flash chromatography (Et₂O/MeOH/NH₄OH//80/20/1) to yield expected compound as a yellow solid (120 mg, 99% yield). LC-MS: m/z (ESI) 452.2 [M+H]⁺.
¹H NMR (300 MHz, MeOH-d₄) δ8.33; (d, J=5.7 Hz, 1H), 8.27; (d, J=9.0 Hz, 1H), 7.85; (d, J=2.1 Hz, 1H), 7.50-7.42; (m, 2H), 7.30-7.21; (m, 2H); 6.81; (d, J=5.7 Hz, 1H), 3.90-3.81; (m, 4H), 3.68; (s, 2H); 3.00-2.90; (m, 4H), 2.70-2.45; (m, 8H), 2.37; (s, 3H); ¹³C NMR (75 MHz, MeOH-d₄) δ152.0; (CH), 151.8; (C), 151.0; (C), 150.0; (C), 136.9; (C), 136.7; (C), 135.3; (C), 127.4; (CH), 127.3; (CH), 126.7; (CH), 124.9; (CH), 124.8; (CH), 122.3; (CH), 119.3; (C), 120.3; (CH), 68.5; (CH₂), 57.9; (CH₂), 55.7; (CH₂), 54.6; (CH₂), 53.1; (CH₂); 28.1; (CH₃).

Example 33

Preparation of N-{3-[(tert-butylamino)methyl]-4-(morpholin-4-yl)phenyl}-7-chloroquinolin-4-amine (compound 88)

To a suspension of {5-[(7-chloroquinolin-4-yl)amino]-2-(morpholin-4-yl)phenyl}methanol hydrochloride (compound of step C of example 31) (0.105 g, 0.26 mmol) in 4 mL of NMP at 0° C. was added thionyl chloride (90 μL, 1.23 mmol). The reaction mixture was warmed up to room temperature and stirred for 3 h. The reaction mixture was then slowly added to tert-butylamine (0.81 mL, 7.75 mmol) in 1 mL of NMP at 0° C. and then stirred at room temperature for 2 h. This solution was diluted in 100 mL of $CH_2Cl_2$ and washed with a saturated aqueous solution of $NaHCO_3$. The organic layer was dried over $MgSO_4$, filtered, evaporated and purified by flash chromatography ($Et_2O$/MeOH/$NH_4$OH//90/10/1 then 80/20/1) to yield expected compound as a yellow solid (103 mg, 92% yield). LC-MS: m/z (ESI) 425.2 [M+H]$^+$.

$^1$H NMR (300 MHz, MeOH-$d_4$) δ8.36; (d, J=5.6 Hz, 1H), 8.29; (d, J=9.0 Hz, 1H), 7.85; (d, J=2.1 Hz, 1H), 7.49; (dd, J=9.1 and 2.4 Hz, 1H), 7.43; (d, J=1.7 Hz, 1H), 7.38-7.30; (m, 2H); 6.91; (d, J=5.6 Hz, 1H), 3.96; (s, 2H), 3.90-3.84; (m, 4H), 3.00-2.95; (m, 4H), 1.30; (s, 9H); $^{13}$C NMR (75 MHz, MeOH-$d_4$) δ152.5; (CH), 151.2; (C), 150.2; (C), 150.1; (C), 138.0; (C), 136.8; (C), 136.0; (C), 127.8; (CH), 127.1; (CH), 126.7; (CH), 125.3; (CH), 124.7; (CH), 123.5; (CH), 119.5; (C), 102.6; (CH), 68.5; ($CH_2$), 54.7; ($CH_2$), 50.8; (C), 43.7; ($CH_2$), 28.1; ($CH_3$).

Example 34

Preparation of 7-chloro-N-[3-({[2-(dimethylamino) ethyl](methyl)amino}methyl)-4-(morpholin-4-yl) phenyl]quinolin-4-amine To a suspension of {5-[(7-chloroquinolin-4-yl)amino]-2-(morpholin-4-yl)phenyl}methanol hydrochloride (compound of step C of example 31) (0.100 g, 0.25 mmol) in 4 mL of NMP at 0° C. was added thionyl chloride (90 μL, 1.23 mmol). The reaction mixture was warmed up to room temperature and stirred for 3 h. The reaction mixture was then slowly added to N,N,N'-trimethylethylenediamine (1 mL, 7.50 mmol) in 1 mL of NMP at 0° C. and then stirred at room temperature for 2 h. This solution was diluted in 100 mL of $CH_2Cl_2$ and washed with a saturated aqueous solution of $NaHCO_3$. The organic layer was dried over $MgSO_4$, filtered, evaporated and purified by flash chromatography (DCM/MeOH/$NH_4$OH//90/10/1 then 80/20/1) to yield expected compound as a yellow solid (97 mg, 85% yield). LC-MS: m/z (ESI) 454.4 [M+H]$^+$.

$^1$H NMR (300 MHz, $CDCl_3$) δ8.50; (d, J=3.0 Hz, 1H), 8.03; (d, J=3.0 Hz, 1H), 7.89; (d, J=9 Hz, 1H), 7.42; (m, 2H), 7.26; (m, 2H), 6.84; (d, J=3.0 Hz, 1H), 3.88-3.85; (m, 4H), 3.68; (s, 2H), 3.00-2.97; (m, 4H), 2.52-2.49; (m, 4H) $^{13}$C NMR (75 MHz, $CDCl_3$-$d_1$) δ152.4; (C), 151.9; (CH), 149.8; (CH), 148.4; (CH), 135.7; (CH), 135.5; (CH), 135.3; (CH), 128.9; (C), 126.0; (C), 125.7; (C), 122.3; (C), 120.6; (C), 118.2; ($CH_2$), 101.8; (C), 67.6; ($CH_2$), 57.2; ($CH_2$), 54.7; ($CH_2$), 53.5; ($CH_3$)

Example 35

Preparation of 7-chloro-N-[4-(morpholin-4-yl)-3-(morpholin-4-ylmethyl)phenyl]quinolin-4-amine (compound 90)

To a suspension of {5-[(7-chloroquinolin-4-yl)amino]-2-(morpholin-4-yl)phenyl}methanol hydrochloride (compound of step C of example 31) (0.100 g, 0.25 mmol) in 4 mL of NMP at 0° C. was added thionyl chloride (90 μL, 1.23 mmol). The reaction mixture was warmed up to room temperature and stirred for 3 h. The reaction mixture was then slowly added to N,N,N'-trimethylethylenediamine (0.65 mL, 7.38 mmol) in 1 mL of NMP at 0° C. and then stirred at room temperature for 2 h. This solution was diluted in 100 mL of $CH_2Cl_2$ and washed with a saturated aqueous solution of $NaHCO_3$. The organic layer was dried over $MgSO_4$, filtered, evaporated and purified by flash chromatography (DCM/MeOH///90/10) to yield expected compound as a yellow solid (83 mg, 77% yield). LC-MS: m/z (ESI) 439.3 [M+H]$^+$.

$^1$H NMR (300 MHz, MeOH-$d_4$) δ8.50; (d, J=3.0 Hz, 1H), 8.03; (d, J=3.0 Hz, 1H), 7.89; (d, J=9.0 Hz, 1H), 7.42; (m, 2H), 7.26; (m, 2H), 6.84; (d, J=3.0 Hz, 1H), 3.88-3.85; (m, 4H), 3.82-3.70; (m, 4H), 3.69; (s, 2H), 3.00-2.97; (m, 4H), 2.52-2.49; (m, 4H), 2.10-1.92; (m, 5H)$^{13}$C NMR (75 MHz, MeOH-$d_4$) δ149.7; (CH), 148.6; (CH), 135.7; (CH), 134.9; (CH), 134.7; (CH), 128.7; (C), 126.3; (C), 125.8; (C), 123.0; (C), 121.4; (C), 117.9; (CH), 67.6; ($CH_2$), 67.2; ($CH_2$), 57.9; ($CH_2$), 53.9; ($CH_2$), 53.5; ($CH_2$).

B—Biological Tests

In Vitro Experiments

Cell Treatment for Cytotoxicity and Western Blotting

The human neuroblastoma cell line SKNSH-SY5Y APP$^{wt}$ is cultured in Dulbecco's modified Eagle medium (Invitrogen) supplemented with 10% fetal calf serum (PAA), 2 mM L-glutamine (Invitrogen), 1 mM non-essential amino acids (Invitrogen), 50 units/ml penicillin/streptomycin (Invitrogen) and 200 μg geneticin (G418; Invitrogen) (selection for cell expressing APP) in a 5% $CO_2$ humidified incubator at 37° C. Cells are seeded into 96-wells plates (20000 cells/well) for cytotoxicity assay and 12-wells plate (300000 cells/well) for western blotting for 18 h.

Compounds are dissolved in pure DMSO at a concentration of 10 mM (Stock Solution) over a silica gel layer under a chemical hood. For cytotoxicity assay, cells are incubated with 100 μl/well of each product at 100; 30; 10; 3; 1; 0.3 and 0.1 μM in a 5% $CO_2$ incubator at 37° C. for 24 h. The number of viable cells is determined with CellTiter 96® Aqueous One solution Reagent (MTS) (Promega) according to the manufacturer protocol. Briefly, 20 μl of this reagent is added to each well and the plate is incubated for 2 hours in a 5% $CO_2$ incubator at 37° C. The absorbance is read at 490 nm. Optical density is analyzed with excel computer program and CC50 determined with Graph Pad Prism (version 4.02) computer program.

For western blotting, cells are incubated with 700 μl/well of each product at 10; 3; 1 and 0.31 μM in a 5% $CO_2$ incubator at 37° C. for 24 h. The following day, culture medium samples are collected for ELISA assay and stored at −80° C. Cells are rinsed very slowly with cold PBS, snap-frozen on dry ice and immediately stored at −80° C.

Innotest β Amyloid 1-42 Innogenetics®

The β-amyloid 1-42 rate is quantified in SY5Y cells-culture medium by using the Innotest β-amyloid 1-42 (80324 Innogenetics®) according to the manufacturer instructions. Briefly, Fresh culture medium is used to dilute the standard. Culture samples are centrifuged at 200 g at 4° C. during 5 minutes in order to eliminate cell fragments.

First, 75 μl of the conjugate working solution1 (3D6 biotinylated antibody) is added to a 21F12 Ab precoated well. Twenty five μl of pure supernatant samples are then added to the coated well, and incubated for 1 h. Then the plate is washed 5 times with the washing buffer. Then 100 μl of peroxidase-labeled streptavidin (conjugate working solution 2) is added and incubated for 30 min at RT. After washing the plate 5 times, 100 µl of tetramethyl benzidine (substrate working solution) is added onto the plate and incubated for 30 minutes in the dark. The reaction is stopped with 50 µl 0.9N sulfuric acid (stop solution). The absorbance is read at 450 nm.

A sigmoidal curve fitting (four parameter polynomial curve) is used to calculate the standard curve. The corresponding concentration of β-amyloid (1-42) in pg/ml is determined from the standard curve. Results are expressed in concentration of β-amyloid in pg per µg of total proteins. Graphs and statistic analyses (t Test) are performed with Graph Pad Prism computer program (V0.5).

In Vivo Experiments

Mice Treatment

Test molecules are intraperitoneally injected to 4 month old C57BI6 females mice either at 12.5; 25; 50 mg/kg or vehicle once, and sacrificed 24 h after by decapitation. Brain is immediately removed and Prefrontal Cortex is dissected by using a cold zinc brain matrix. The total dissection time was <3 min from decapitation. Following dissection tissue is frozen in dry ice and then stored at −80° C. for western blotting.

Protein Extraction and Western Blotting Analysis

Cells in twelve-well plates are collected in 50 µl Laemmli Lysis Buffer (pH 6.8, 50 mM Tris Base, 2% SDS, 20% Glycerol, 1 mM sodium pyrophosphate, 1 mM sodium orthovanadate and Protease Inhibitor Cocktail Complete Mini-Roche) per well. Cells are scrapped and lysates sonicated for 5 min.

Protein extracts of Prefrontal Cortex samples are prepared in 50 µl Laemmli Lysis Buffer (pH 6.8, 50 mM Tris Base, 2% SDS, 20% Glycerol, 1 mM sodium pyrophosphate, 1 mM sodium orthovanadate and Protease Inhibitor Cocktail Complete Mini-Roche) by trituration of the fragments in a 0.2 ml glass micro tissue grinder. The tissue lysates are sonicated for 5 min, then passed through a 26 gauge needle and rocked for 1 h at 4° C. Samples are then cleared by centrifugation at 200 g for 5 min.

Protein content is determined using the BCA Method (Pierce). Samples containing equal amounts of protein (35 µg total protein for mice and 20 µg total protein for cells per well) are heated at 85° C. for 2 min after thawing and electrophoresed for 2.45 h at 125 V in a 16% Tricine precast gels according to the protocol supplied with the NuPAGE system (Invitrogen). After size fractionation, the proteins are transferred onto nitrocellulose 0.2 µm pore-size membranes (Invitrogen) in the blot module of the NuPAGE sytem for 1 h at room temperature (RT). Blots are blocked for 1 h in TNT with 0.05% Tween 20 and 5% nonfat milk at RT, incubated overnight at 4° C. with anti-C term APP C1:3-2429 (1:250000) primary antibody and washed four times with TNT before being exposed to peroxidase labeled anti-mouse IgG (H+L) C4 94010 (1:50000; Vector) secondary antibody for 45 h at 25° C. The immunoreactions are detected with SuperSignal West Pico Chemiluminescent Substrate (Thermo specific, 34077). Images are scanned with LAS-3000 Image System (Global FUJIFILM) and bands quantified by ImageJ 1.37v computer program. The different APP-CTF bands are detected as a function of their molecular mass, as described in Vingtdeux, V., Hamdane, M., Gompel, M. et al. (2005) Phosphorylation of amyloid precursor carboxy-terminal fragments enhances their processing by a gamma-secretase-dependent mechanism. *Neurobiol Dis*, 20, 625-637. Graphs and statistical analysis of results is performed with Graph Pad Prism (version 4.02) computer program.

The full biological results are given below (for known compounds as wall as for new compounds of examples 1 to 23 as mentioned above) (see also FIG. 1 for in vivo results).

Biological Results of Compounds Having Formula (I-4-1)

| N° | Ref | Ref lab | $R_6$ | $NR_1R_2$ | CTFalpha 1 µM* | AICD 1 µM* | $CC_{50}$ µM MRC-5 (SY5Y) |
|---|---|---|---|---|---|---|---|
| 1 | EP-29 | EP985 | H | $NEt_2$ | 1119 | 413 | 31.3 ± 0.8 |
| 3 | EP-23 | EP637 | OEt | $NEt_2$ | 3071 | 129 | — |
| 4 | EP-30 | EP537 | H | pyrrolidine | 1065 | 378 | 29.8 ± 6.2 |

*results in arbitrary units compared to a control with a value of 100

Biological Results of Compounds Having Formula (I-4-2)

| N° | Ref | Ref lab | $R_6$ | $NR_1R_2$ | CTFα 1 µM* | AICD 1 µM* | $CC_{50}$ µM MRC-5 |
|---|---|---|---|---|---|---|---|
| 13 | EPC-9g $ | EP987 | pF—$C_6H_4$— | $NEt_2$ | 1560 | 176 | 17.4 ± 0.2 |
| 19 | EPC-9m $ | EP671 | Et | $NEt_2$ | 1349 | 194 | 18.1 ± 1.2 |
| 20 | EPC-9n $ | EP1031 645 | $pCF_3O$—$C_6H_4$— | $NEt_2$ | 1880 | 150 | 18.6 ± 0.8 |
| 34 | EPC-101 $ | EP517 | Me | pyrrolidine | 1040 | 332 | 21.3 ± 3.4 |
| 35 | EPC-10m | EP541, 441 | Et | pyrrolidine | 1665 | 328 | 18.9 ± 3.8 |

*results in arbitrary units compared to a control with a value of 100

Biological Results of Compounds Having Formula
(I-4-3)

| N° | Ref | Ref lab | NR$_a$R$_b$ | NR$_1$R$_2$ | Aβ 1 μM* | CTFα 1 μM* | AlCD 1 μM* | CC$_{50}$ μM MRC-5 |
|---|---|---|---|---|---|---|---|---|
| 42 | EPN-7d | EP573 | morpholine | NEt$_2$ | 90 | 155 | 189 | 16.7 ± 0.2 |
| 47 | EPN-8a | EP977 | dimethylamine | pyrrolidine | 15 | 109 | 130 | 14.7 ± 1.2 |
| 50 | EPN-8d | EP577 | morpholine | pyrrolidine | 55 | 311 | 201 | 31.8 ± 0.9 |
| 51 | EPN-8e | EP867 | N-methyl-piperazine | pyrrolidine | 47 | 3569 | 1295 | 8.6 ± 0.8 (<5) |
| 54 | EPN-8h | EP1101 | piperidinethylamine | pyrrolidine | 30 | 1422 | 343 | 2.1 ± 0.1 |

*results in arbitrary units compared to a control with a value of 100

Biological Results of Compounds Having Formula
(I-5)

| N° | Ref | Ref lab | R$_5$ | NR$_a$R$_b$ | NR$_1$R$_2$ | Aβ 1 μM* | CTFα 1 μM* | AlCD 1 μM* |
|---|---|---|---|---|---|---|---|---|
| 56 | 12b | NLF54 | H | N—Me piperazine | NHtBu | 45 | 183 | 823 |
| 57 | 15b | NLF72 | H | N—Me piperazine | Morpholine | 19 | 194 | 757 |
| 59 | 23a | NLF45 | CH$_3$ | N—Me piperazine | Pyrrolidine | 73 | 629 | 325 |

*results in arbitrary units compared to a control with a value of 100

Biological Results of Compounds Having Formula
(I-6)

| N° | Ref | Ref lab | X | R$_5$ | NR$_1$R$_2$ | Aβ 1 μM* | CTFα 1 μM* | AlCD 1 μM* |
|---|---|---|---|---|---|---|---|---|
| 64 | 2c | EB344(2) | CO | H | dimethyl[3-(piperazin-1-yl)propyl]amine | 31 | 106 | 669 |
| 66 | 8 | FD15 | CH$_2$ | OH | Pyrrolidine | 19 | 754 | 886 |

*results in arbitrary units compared to a control with a value of 100

Biological Results of Compounds Having Formula
(I-7)

| N° | Ref | Ref lab | NR$_1$R$_2$ | Aβ 1 μM* | CTFα 1 μM* | AlCD 1 μM* |
|---|---|---|---|---|---|---|
| 69 | 3c | EB344(1) | dimethyl[3-(piperazin-1-yl)propyl]amine | 46 | 126 | 302 |

*results in arbitrary units compared to a control with a value of 100

Biological Results of Compounds Having Formula
(I-8)

| N° | Ref | Ref lab | R$_6$ | NR$_1$R$_2$ | Aβ 1 μM* | CTFα 1 μM* | AlCD 1 μM* |
|---|---|---|---|---|---|---|---|
| 70 | 20a | EB551 | N—Me piperazine | N—Me piperazine | — | 687 | 515 |
| 72 | 21 | EB546 | OH | N—Me piperazine | 100 | 105 | 80 |

*results in arbitrary units compared to a control with a value of 100

Biological Results of Compounds Having Formula (I-13)

| N° | Ref | Ref lab | structure | Aβ 1 μM* | CTFα 1 μM* | AlCD 1 μM* |
|---|---|---|---|---|---|---|
| 74 | 3 | EB358a | (structure) | 44 | 4016 | 1933 |
| 76 | 5 | EB418 | (structure) | 76 | 2618 | 1503 |
| 77 | 7 | EB374 | (structure) | 85 | 1868 | 618 |

*results in arbitrary units compared to a control with a value of 100

Biological Results of Compounds Having Formula (I-9)

| N° | Ref | Ref lab | NR$_1$R$_2$ | Aβ 1 μM* | CTFα 1 μM* | AlCD 1 μM* | CC$_{50}$ μM MRC-5 |
|---|---|---|---|---|---|---|---|
| 80 | 40 | MAD1342 | NMe(CH$_2$)$_2$NMe$_2$ | 55 | 570 | 1226 | <10 |
| 83 | 43 | SD5/4 | NH(CH$_2$)$_2$Nmorpholine | 80 | 286 | 135 | <10 |
| 84 | 44 | SD4/54 | NEt$_2$ | 60 | 358 | 209 | <10 |
| 86 | 47 | SD4/35 | N(pyrrolidine) | 30 | 856 | 664 | <10 |
| 87 | 48 | SD4/14 | N(piperazine)N—Me | 40 | 1019 | 255 | <10 |
| 91 | 52 | SD4/36 | N(piperazine)N—Ph | 25 | 884 | 286 | <10 |
| 95 | 56 | SD4/73 | N(piperazine)N—CH$_2$—pOMePh | 45 | 693 | 191 | <10 |
| 101 | 62 | MAD1338 | NHCH$_2$Ph | 20 | 315 | 329 | <10 |
| 103 | 64 | SD4/78 | NHCH$_2$—pClPh | 20 | 186 | 133 | <10 |

*results in arbitrary units compared to a control with a value of 100

Biological Results of Compounds Having Formula (I-10)

| N° | Ref | Ref lab | NR₁R₂ | Aβ 1 μM* | CTFα 1 μM* | AlCD 1 μM* |
|---|---|---|---|---|---|---|
| 107 | 5 | SD5/56 | N(morpholine) | 25 | 1013 | 450 |

*results in arbitrary units compared to a control with a value of 100

Biological Results of Compounds Having Formula (I-10)

| N° | Ref | Ref lab | NR₁R₂ | Aβ 1 μM* | CTFα 1 μM* | AlCD 1 μM* | CC₅₀ μM MRC-5 |
|---|---|---|---|---|---|---|---|
| 109 | 10 | MAD1328 | NHCH₂CH₂CH₂NMe₂ | 75 | 100 | 100 | >32 |
| 110 | 12 | MAD1420 | NHCH₂CH₂Npyrrolidine | 80 | 131 | 143 | 17 |

*results in arbitrary units compared to a control with a value of 100

Biological Results of Compounds Having Formula (I-12)

| N° | Ref | Ref lab | NR₁R₂ | Aβ 1 μM* | CTFα 1 μM* | AlCD 1 μM* | CC₅₀ μM MRC-5 |
|---|---|---|---|---|---|---|---|
| 113 | 2 | SD4/18 | NH (CH₂)₂N-morpholine | 80 | 77 | 170 | >12.5 |
| 114 | 3 | SD3/34 | NH(CH₂)₃NEt₂ | 70 | 240 | 203 | 6 |

*results in arbitrary units compared to a control with a value of 100

In Vivo Results of Compound 66 (See Example 12)

FIG. 1 represents the evolution of CTF-alpha and CTF-beta fragments by C57B16 female mice to which either 12.5, 25, 50 mg/kg of compound 66 or only the vehicle was injected (control). The results show the optical density (in arbitrary units) for each mouse. FIG. 1 shows that compound 66 increases the production of APP-CTFα.

The invention claimed is:

1. A method of treating a neurodegenerative disease involving formation of amyloid plaques and/or where a dysfunction of the APP metabolism occurs in a patient in need thereof, comprising the step of
administering to said patient a therapeutically effective amount of a compound having formula (I):

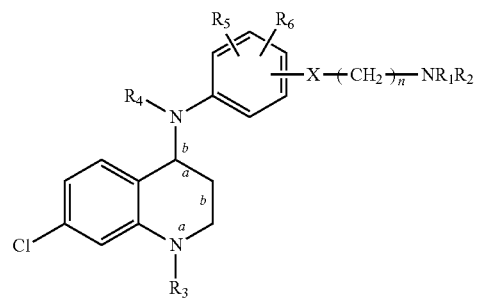

(I)

wherein:
a represents a single bond or a double bond;
b represents a single bond or a double bond, provided that when a is a single bond, then b is a double bond, and when a is a double bond, then b is a single bond;
$R_3$ is absent when a is a double bond, or, when a is a single bond, $R_3$ is chosen from the groups consisting of: alkyl, cycloalkyl, aryl and heterocycle radicals, said alkyl, cycloalkyl, aryl and heterocycle radicals being substituted or unsubstituted;
$R_4$ is absent when b is a double bond, or, $R_4$ is H when b is a single bond;

$R_5$ is chosen from the group consisting of:
H,
$(C_1$-$C_{12})$alkyl,
OH, and
$(C_1$-$C_{12})$alkoxy,
$R_6$ is chosen from the group consisting of:
H,
halogen,
CN,
OH,
$(C_1$-$C_{12})$alkoxy,
$(C_1$-$C_{12})$alkyl,
$(C_6$-$C_{30})$aryl,
heteroaryl,
$CO_2R$, wherein R is an alkyl group comprising from 1 to 12 carbon atoms,
$NR_aR_b$, $R_a$ and $R_b$ being each independently chosen from: H, alkyl, aralkyl, aryl, cycloalkyl, and heterocycle groups, said alkyl, aralkyl, aryl, cycloalkyl, and heterocycle groups being substituted or unsubstituted, or $R_a$ and $R_b$ forming together with the nitrogen atom carrying them a substituted or unsubstituted heterocycle group; and
a radical of formula: —X'—$(CH_2)_{n'}$—$NR'_1R'_2$,
wherein:
X' is chosen from: $CH_2$, O, NH, CO, $CH_2OCO$, and NHCO;
n' is 0, 1 or 2;
$R'_1$ and $R'_2$ are each independently chosen from H, alkyl, aralkyl, aryl, cycloalkyl and heterocycle groups, said alkyl, aralkyl, aryl, cycloalkyl, and heterocycle groups being substituted or unsubstituted, or $R'_1$ and $R'_2$ may form together with the nitrogen atom carrying them a substituted or unsubstituted heterocycle group;

X is chosen from: CH$_2$, O, NH, CO, CH$_2$OCO, and NHCO;

n is 0, 1 or 2;

R$_1$ and R$_2$ are each independently chosen from H, alkyl, aralkyl, aryl, cycloalkyl and heterocycle groups, said alkyl, aralkyl, aryl, cycloalkyl and heterocycle groups being substituted or unsubstituted, or R$_1$ and R$_2$ may form together with the nitrogen atom carrying them a substituted or unsubstituted heterocycle group;

or its pharmaceutically acceptable salts, hydrates or hydrated salts or its polymorphic crystalline structures, racemates, diastereisomers or enantiomers, with the exclusion of the compounds having the following formula:

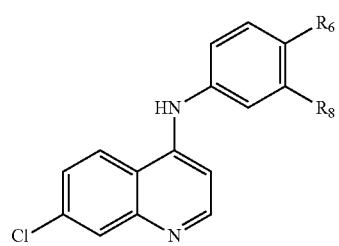

wherein:
R$_6$ is H and R$_8$ is —CH$_2$—NEt$_2$;
R$_6$ is OH and R$_8$ is chosen from: —CH$_2$—NEt$_2$, —CH$_2$—NHEt,

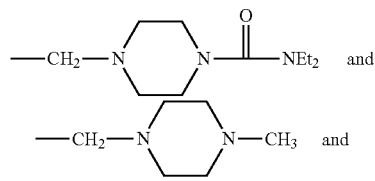

R$_6$ is OMe and R$_8$ is —CH$_2$—NEt$_2$ or

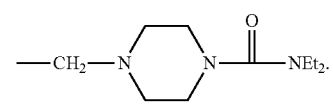

2. The method of claim 1, wherein said compound has formula (I-1):

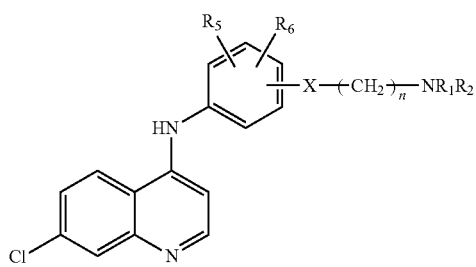

wherein R$_1$, R$_2$, R$_5$, R$_6$, X, and n are as defined in claim 1.

3. The method of claim 1, wherein said compound has formula (I-2):

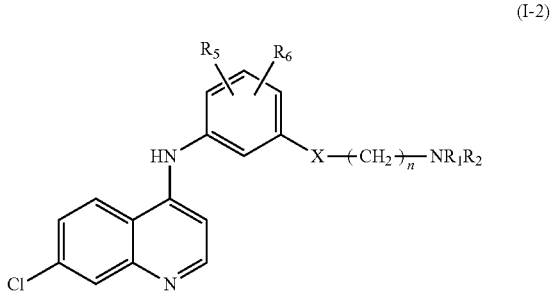

wherein R$_1$, R$_2$, R$_5$, R$_6$, X, and n are as defined in claim 1.

4. The method of claim 1, wherein said compound has formula (I-3):

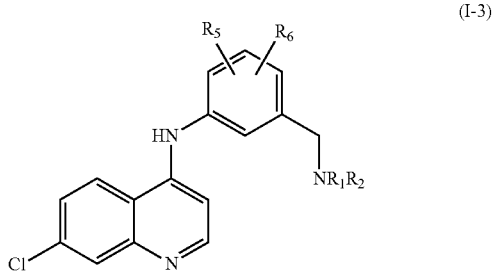

wherein R$_1$, R$_2$, R$_5$, and R$_6$ are as defined in claim 1.

5. The method of claim 1, wherein said compound has formula (I-4):

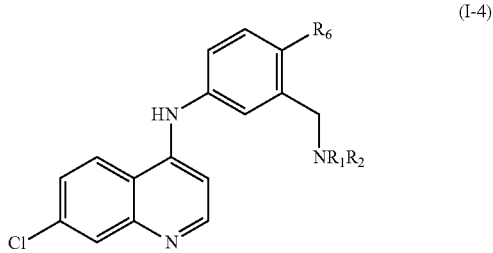

wherein R$_1$ and R$_2$ are as defined in claim 1, and R$_6$ is chosen from: H, halogen, OH, (C$_1$-C$_{12}$)alkoxy, (C$_1$-C$_{12}$)alkyl, (C$_6$-C$_{30}$)aryl, heteroaryl, and NR$_a$R$_b$, and R$_a$ and R$_b$ are as defined in claim 1.

6. The method of claim 1, wherein said compound has formula (I-5):

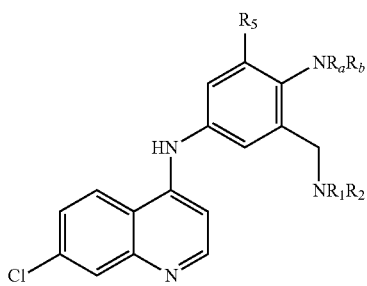

(I-5)

wherein $R_1$, $R_2$, $R_5$, $R_a$ and $R_b$ are as defined in claim 1.

7. The method of claim 1, wherein said compound has formula (I-6):

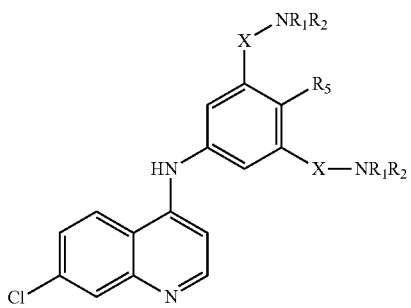

(I-6)

wherein $R_1$, $R_2$ and $R_5$ are as defined in claim 1,
and wherein X is CO or $CH_2$.

8. The method of claim 1, wherein said compound has formula (I-7):

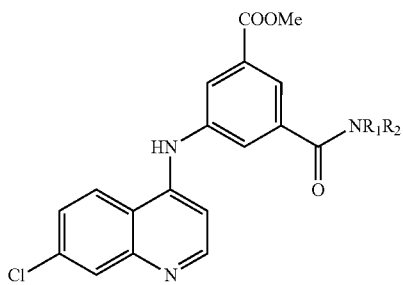

(I-7)

wherein $R_1$ and $R_2$ are as defined in claim 1.

9. The method of claim 1, wherein said compound has formula (I-8):

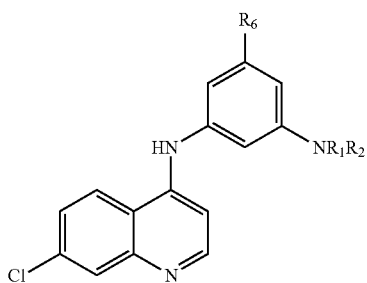

(I-8)

wherein $R_1$ and $R_2$ are as defined in claim 1, and form, together with the nitrogen atom carrying them, a heterocycle,
and $R_6$ is as defined in claim 1.

10. The method of claim 1, wherein said compound has formula (I-9):

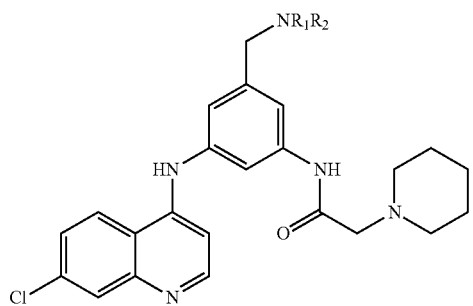

(I-9)

wherein $R_1$ and $R_2$ are as defined in claim 1.

11. The method of claim 1, wherein said compound has formula (I-10):

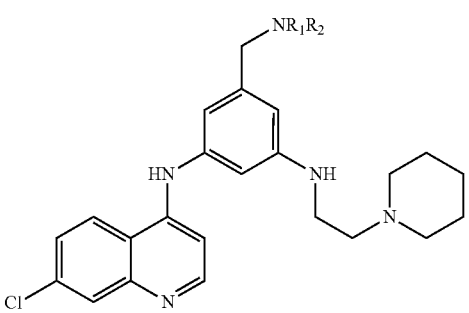

(I-10)

wherein $R_1$ and $R_2$ are as defined in claim 1.

12. The method of claim 1, wherein said compound has formula (I-11):

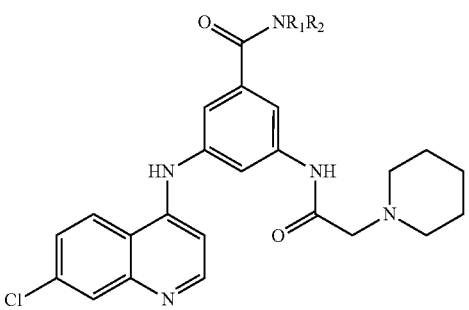

(I-11)

wherein $R_1$ and $R_2$ are as defined in claim 1.

13. The method of claim 1, wherein said compound has formula (I-12):

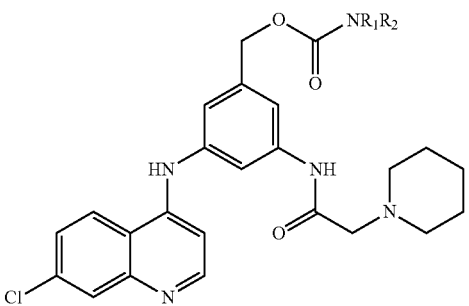

(I-12)

wherein $R_1$ and $R_2$ are as defined in claim 1.

14. The method of claim 6, wherein $R_5$ is H or $CH_3$.

15. The method of claim 6, wherein $R_a$ and $R_b$ form, with the nitrogen atom carrying them, a substituted or unsubstituted heterocycle group.

16. The method of claim 15, wherein $R_a$ and $R_b$ form with the nitrogen atom carrying them a N-methylpiperazine or a morpholine group.

17. The method of claim 7, wherein $R_5$ is H or OH.

* * * * *